(12) United States Patent
Tsuruno

(10) Patent No.: US 9,398,897 B2
(45) Date of Patent: Jul. 26, 2016

(54) ULTRASONIC SENSOR, MEASURING DEVICE, AND MEASUREMENT SYSTEM

(71) Applicant: SEIKO EPSON CORPORATION, Tokyo (JP)

(72) Inventor: Jiro Tsuruno, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 162 days.

(21) Appl. No.: 14/107,637

(22) Filed: Dec. 16, 2013

(65) Prior Publication Data

US 2014/0180115 A1    Jun. 26, 2014

Related U.S. Application Data

(63) Continuation of application No. 13/165,919, filed on Jun. 22, 2011, now Pat. No. 8,679,022.

(30) Foreign Application Priority Data

Jun. 25, 2010   (JP) ................. 2010-145106

(51) Int. Cl.
*A61B 8/00*     (2006.01)
*A61B 8/04*     (2006.01)
*A61B 8/06*     (2006.01)

(52) U.S. Cl.
CPC .......... *A61B 8/4477* (2013.01); *A61B 8/04* (2013.01); *A61B 8/06* (2013.01); *A61B 8/4227* (2013.01); *A61B 8/4461* (2013.01); *A61B 8/4483* (2013.01); *A61B 8/4472* (2013.01)

(58) Field of Classification Search
CPC .......... A61B 8/04; A61B 8/06; A61B 8/4227; A61B 8/4461; A61B 8/4472
See application file for complete search history.

(56) References Cited

U.S. PATENT DOCUMENTS

| | | | | |
|---|---|---|---|---|
| 5,854,450 A | * | 12/1998 | Kent ..................... | G06F 3/0418 178/18.01 |
| 6,159,149 A | * | 12/2000 | Erikson et al. ............... | 600/437 |
| 6,503,204 B1 | * | 1/2003 | Sumanaweera ....... | B06B 1/0622 29/25.35 |
| 7,872,399 B2 | * | 1/2011 | Kondou et al. .............. | 310/334 |
| 8,310,133 B2 | * | 11/2012 | Brown .................. | B06B 1/0622 310/334 |
| 2005/0020918 A1 | * | 1/2005 | Wilk et al. .................. | 600/439 |
| 2005/0020919 A1 | | 1/2005 | Stringer et al. | |
| 2006/0219013 A1 | | 10/2006 | Baba et al. | |

(Continued)

FOREIGN PATENT DOCUMENTS

| JP | 2001-521404 A | 11/2001 |
|---|---|---|
| JP | 2002-011008 A | 1/2002 |

(Continued)

*Primary Examiner* — Baisakhi Roy
(74) *Attorney, Agent, or Firm* — Global IP Counselors, LLP

(57) ABSTRACT

An ultrasonic sensor includes a substrate, three or more ultrasonic arrays and a control unit. The three or more ultrasonic arrays are disposed on a surface of the substrate. The control unit is configured to control ultrasonic waves transmitted from the ultrasonic arrays. Each of the three or more ultrasonic arrays includes a linear array structure has a plurality of ultrasonic elements arranged in a corresponding one of three or more straight lines, with the three or more straight lines collectively enclosing a closed area on a plane that contains the surface of the substrate. The control unit is configured to control the ultrasonic waves transmitted from each of the three or more ultrasonic arrays so that the ultrasonic waves are transmitted within a scanning plane that contains the corresponding one of the three or more straight line and that is perpendicular to the surface of the substrate.

16 Claims, 18 Drawing Sheets

(56) References Cited

U.S. PATENT DOCUMENTS

| | | | |
|---|---|---|---|
| 2008/0062151 A1* | 3/2008 | Kent | G06F 3/0418 345/177 |
| 2009/0199392 A1* | 8/2009 | Singh et al. | 29/594 |
| 2010/0117993 A1* | 5/2010 | Kent | G06F 3/0436 345/177 |
| 2010/0268089 A1* | 10/2010 | Degertekin | 600/467 |

FOREIGN PATENT DOCUMENTS

| | | |
|---|---|---|
| JP | 2005-034543 A | 2/2005 |
| JP | 2009-201557 A | 9/2009 |
| JP | 2010-244119 A | 10/2010 |
| JP | 2011-038915 A | 2/2011 |
| WO | 97/32277 A1 | 9/1997 |

* cited by examiner

ULTRASONIC SENSOR, MEASURING DEVICE, AND MEASUREMENT SYSTEM

CROSS-REFERENCE TO RELATED APPLICATIONS

This application is a continuation application of U.S. patent application Ser. No. 13/165,919 filed on Jun. 22, 2011. This application claims priority to Japanese Patent Application No. 2010-145106 filed on Jun. 25, 2010. The entire disclosures of U.S. patent application Ser. No. 13/165,919 and Japanese Patent Application No. 2010-145106 are hereby incorporated herein by reference.

BACKGROUND

1. Technical Field

The present invention relates to an ultrasonic sensor, a measuring device, and a measurement system able to detect the position of an object to be detected using ultrasound.

2. Related Art

There are devices that use ultrasound to detect the state of an object to be detected such as a blood vessel in the human body (e.g., see Japanese Laid-Open Patent Application Publication No. 2005-34543).

The device described in Japanese Laid-Open Patent Application Publication No. 2005-34543 has a probe in which a transducer has been disposed longitudinally parallel to the axial direction of a blood vessel. From the probe, a blood vessel diameter-detecting ultrasonic beam is transmitted vertically with respect to the wall of the blood vessel and a speed-detecting ultrasonic beam is transmitted so as to intersect the axial direction of the blood vessel at an angle in order to measure the change in the blood vessel diameter and the blood flow over time.

However, in a device such as the one described in Japanese Laid-Open Patent Application Publication No. 2005-34543, the position of the blood vessel has to be accurately identified and the axial direction of the blood vessel has to be aligned with the direction of the transducer when blood flow and blood pressure are measured. If the user is a person with specialized knowledge such as a physician, the position of the blood vessel can be easily identified. However, it cannot be easily identified if the user is a person without specialized knowledge. Therefore, such a device is difficult to operate correctly if the user is a person without specialized knowledge, even though it can be easily operated by a person with specialized knowledge. When the condition of a blood vessel is to be measured continuously for 24 hours, the position of the blood vessel may shift. In these situations, the direction of the transducer cannot be set with respect to the axial direction of the blood pressure, and accurate measurement results cannot be obtained.

In response, a method for identifying the position of an object to be measured (e.g., see Japanese Laid-Open Patent Application Publication No. 2002-11008) and a method for measuring displacement of a blood vessel (e.g., see Japanese Laid-Open Patent Application Publication No. 2009-201557) have been proposed.

The device described in Japanese Laid-Open Patent Application Publication No. 2002-11008 is equipped with an ultrasonic probe in which transducers for detecting the position of a blood vessel are arranged in a two-dimensional array. In this device, ultrasound is transmitted directly below the transducers for detecting the position of a blood vessel, and ultrasound reflected by the blood vessel directly below the ultrasonic probe is detected to measure the position of the blood vessel.

In the configuration of the device described in Japanese Laid-Open Patent Application Publication No. 2009-201557, a single transducer is arranged on both ends of a probe for measuring blood flow to test for the position of maximum blood flow, and detect the position of the blood vessel.

SUMMARY

However, in order to detect the position of a blood vessel using the device described in Japanese Laid-Open Patent Application Publication No. 2002-11008, the blood vessel has to be positioned directly below the transducers arranged in an array for detecting the position of the blood vessel. In the device described in Japanese Laid-Open Patent Application Publication No. 2009-201557, the blood vessel has to be positioned directly below a single oscillator. Therefore, transducers for detecting the position of a blood vessel or a single transducer has to be arranged over the entire surface of the probe in order to detect the position of a blood vessel directly below the probe surface. As a result, the configuration is complicated and increases manufacturing costs. The use of a two-dimensional array sensor in which ultrasonic transducers are arranged equally in the X and Y directions has been considered for detecting the position of a blood vessel. However, in such applications as well, the wiring configuration for the ultrasonic transducers in the two-dimensional array is complicated and increases manufacturing costs.

In view of the problem described above, an object of the present invention is to provide an ultrasonic sensor, measuring device, and measurement system able to detect the position of an object to be detected using a simple configuration.

An ultrasonic sensor according to one aspect of the present invention includes a probe surface, a plurality of ultrasonic arrays and a delay control unit. The ultrasonic arrays are disposed on the probe surface. The delay control unit is configured to control a transmission angle of ultrasonic waves transmitted from the ultrasonic arrays. Each of the ultrasonic arrays includes a linear array structure having a plurality of ultrasonic elements arranged in a linear scanning direction. The delay control unit is configured to control the transmission angle of the ultrasonic waves transmitted from the ultrasonic arrays by controlling a timing for transmitting the ultrasonic waves from each of the ultrasonic elements among the plurality of ultrasonic elements. At least two of the ultrasonic arrays among the plurality of ultrasonic arrays disposed on the probe surface have mutually different linear scanning directions in which the plurality of ultrasonic elements are arranged, and the at least two of the ultrasonic arrays are arranged in positions spaced apart from each other.

The configurations of the ultrasonic array described above may include not only a configuration in which a plurality of ultrasonic elements able to both transmit and receive ultrasonic waves are disposed, but, for example, a configuration in which one or more ultrasonic elements for transmitting ultrasonic waves and one or more ultrasonic elements for receiving ultrasonic waves can be disposed in a single ultrasonic array, or a configuration in which both an ultrasonic array for transmitting ultrasonic waves and an ultrasonic array for receiving ultrasonic waves can be disposed in the ultrasonic sensor.

In the ultrasonic sensor as described above, a plurality of ultrasonic arrays is arranged on the probe surface with different linear scanning directions and in different positions. These ultrasonic arrays have a linear array structure in which a plurality of ultrasonic elements is arranged in a linear scanning direction. Also, a delay control unit changes the transmission angle of the ultrasonic waves by delaying the timing for driving the various ultrasonic elements. Therefore, when the ultrasonic elements in the ultrasonic array are connected so that the scanning line is in the same direction as the linear scanning direction, the ultrasonic array can transmit while changing the angle of the ultrasonic waves passing along the scanning line within a plane perpendicular to the probe surface. When the position of an object to be detected is measured, the zone in which the ultrasonic waves transmitted from the ultrasonic arrays are propagated substantially as plane waves (the so-called Fresnel zone) is the scan area. However, by changing the transmission angle of the ultrasonic waves as mentioned above, a fan-shaped scan area centered on an ultrasonic array can be formed. In this case, an object to be detected can be detected in a broader area not just in the area directly below the ultrasonic array.

In the ultrasonic sensor, two or more ultrasonic arrays are disposed on the probe surface, and the position of an object to be detected can be easily detected using these two ultrasonic arrays.

In other words, when the object to be detected has a shape that has an axial direction, including a tubular shape such as a blood vessel in the human body or a rod shape, the presence of the object to be detected can be predicted in a linear direction connecting two points if those two position coordinates are known. When the axial direction of the object to be detected does not change very much in a small volume area, the object to be detected can be considered to be located along a straight line connecting the two points measured by the two ultrasonic arrays.

Therefore, the ultrasonic sensor as described above can obtain two reflection positions at which ultrasonic waves were reflected by transmitting ultrasonic waves from two ultrasonic arrays and receiving the reflection waves. The information from these reflection positions can be used to identify the position and axial direction of an object to be measured. In this ultrasonic sensor, ultrasonic arrays and ultrasonic elements do not have to be packed in over the entire probe surface, and the position of an object to be detected can be detected using a simple configuration.

In the ultrasonic sensor as described above, three or more ultrasonic arrays are preferably arranged on the probe surface, and a closed area surrounded by the linear scanning directions of the ultrasonic arrays is formed on the probe surface.

In this arrangement, a closed area surrounded by the linear scanning directions of three or more ultrasonic arrays is formed on the probe surface. In this case, when an object to be detected with an axial orientation is positioned so as to pass through a volume area directly below the closed area, at least two of the three or more ultrasonic arrays forming the closed area can reliably detect the positions of both ends of the object to be detected.

In the ultrasonic sensor as described above, the probe surface is preferably formed in a polygonal shape, at least one ultrasonic array is preferably arranged on a part of each of sides of the probe surface, and the at least one ultrasonic array is preferably arranged such that the linear scanning direction is parallel to a direction of a corresponding one of the sides of the polygonal shape.

In this arrangement, ultrasonic arrays are disposed on each side of the probe surface. Also, the linear scanning directions of these ultrasonic arrays are parallel to the linear direction of the corresponding sides. Thus, the closed area surrounded by the scanning lines along the linear scanning directions is the entire probe surface. When, as in the ultrasonic sensor described above, an object to be detected with an axial orientation is positioned so as to pass through a volume area directly below the closed area, at least two of the ultrasonic arrays forming the closed area can reliably detect the object to be detected at two points. Therefore, an object to be detected can be reliably detected at a position directly below the probe surface.

Also, an ultrasonic array can be formed in a portion of each side, and wiring for communicating with the ultrasonic arrays is formed in the remaining portion. Thus, the wiring is easier to form than when ultrasonic elements are formed over the entire surface of the probe. In this configuration, another sensor element or circuit can be formed in the center of the probe surface.

Here, in the ultrasonic sensor as described above, at least two of the ultrasonic arrays are preferably arranged apart from each other with respect to each of the sides of the probe surface.

As mentioned above, a delay control unit can adjust the transmission angle of the ultrasonic waves from the ultrasonic arrays along the linear scanning direction, and a fan-shaped scan area is formed in a plane perpendicular to the probe surface through which the scanning line passes. Thus, the scan range can be widened by arranging a plurality of ultrasonic arrays apart from one another on each side of the probe surface. For example, a large area encompassing all of the sides can be used as the scan area, and objects to be detected located within this wider area can be detected by a few of the ultrasonic arrays.

Because the ultrasonic arrays are arranged apart from one another, wiring can be formed in the spaces between the ultrasonic arrays. For example, when another sensor or circuit has to be formed in the center of the probe surface, the wiring pattern can be formed in the space between ultrasonic arrays.

According to the ultrasonic sensor as described above, each of the ultrasonic arrays preferably includes the ultrasonic elements arranged in the linear scanning direction, and the ultrasonic elements includes a plurality of ultrasonic transducers arranged in a perpendicular scanning direction that is perpendicular to the linear scanning direction, the ultrasonic transducers being configured and arranged to transmit ultrasonic waves at different timings, and the ultrasonic waves are preferably delayed and transmitted from the ultrasonic transducers that are arranged on both ends in the perpendicular scanning direction among the plurality of the ultrasonic transducers, and towards the ultrasonic transducer arranged in the center of the perpendicular scanning direction.

In this arrangement, the ultrasonic elements are formed from a plurality of ultrasonic transducers arranged along the perpendicular scanning direction. In this configuration, the timing for transmitting ultrasonic waves from the ultrasonic transducers can be varied, and the ultrasonic wave transmission timing can be delayed from the outer ends towards the center so as to focus the ultrasonic waves towards a predetermined focal point. Here, the ultrasonic waves transmitted from the ultrasonic elements can broaden the Fresnel zone in which plane waves are substantially transmitted, and the distance which the ultrasonic waves are propagated from the ultrasonic element as plane waves can be increased. This scan area can be extended a greater distance from the ultrasonic arrays.

Here, in the ultrasonic sensor as described above, the delay control unit is preferably configured to delay the timings at which the ultrasonic waves are transmitted from the ultrasonic transducers arranged at both ends in the perpendicular scanning direction towards the ultrasonic transducer arranged in the center among the plurality of the ultrasonic transducers arranged along the perpendicular scanning direction.

When a plurality of ultrasonic transducers is arranged in the perpendicular scanning direction as described above, the Fresnel zone can be enlarged and the propagation distance of the plane waves can be extended by delaying the ultrasonic wave transmission timing from both ends towards the center. The delay period is preset and delay drive signals are transmitted using a predetermined delay circuit. However, in the ultrasonic sensor as described above, the Fresnel zone can be controlled by controlling the delay period using a delay control circuit. Here, the delay period can be switched as appropriate by the delay control circuit, for example, based on the distance from the ultrasonic sensor to the object to be detected. For example, during in vivo blood vessel detection, when the object to be detected is a blood vessel in a finger which is a short distance from the skin, the ultrasonic wave transmission timing from the ultrasonic transducers is nearly the same. When the object to be detected is a blood vessel in an arm or leg which is a long distance from the skin, the timing of ultrasonic wave transmission from the ultrasonic transducers can be delayed further to enlarge the Fresnel zone and extend the propagation distance in which the ultrasonic waves are plane waves.

A measuring device according to another aspect of the present invention includes the ultrasonic sensor described above.

As mentioned above, the ultrasonic sensor is able to detect the position of an object to be detected using a simple configuration which reduces manufacturing costs. The manufacturing costs of a measuring device using this ultrasonic sensor can also be reduced.

The measuring device as described above preferably further includes a drive array switching unit configured to switch the ultrasonic arrays among the plurality of ultrasonic arrays into which and from which ultrasonic waves are inputted and outputted, a reflection position calculating unit configured to calculate a reflection position at which the ultrasonic waves are reflected based on reflected ultrasonic waves detected by the ultrasonic arrays, and a position calculating unit configured to calculate the position of an object to be detected from the reflection position detected by the reflection position calculating unit.

In this arrangement, the measurement apparatus uses a drive array switching unit to switch the driven ultrasonic array among two or more ultrasonic arrays in the ultrasonic sensor. This avoids problems such as noise when ultrasonic waves transmitted from another ultrasonic array are inputted. Under the control of the delay control unit, ultrasonic waves are transmitted from the ultrasonic array and reflected by the object to be detected. The reflection waves are received by the ultrasonic array, and electric signals (reception signals) are transmitted based on the reflected ultrasonic waves received by the ultrasonic array. The reflection position calculating unit calculates the point at which the ultrasonic waves were reflected based on the transmission angle of the ultrasonic waves when the reception signals were received, and on the period of time from the transmission of the ultrasonic waves until the reflection waves were received.

In the measuring device, the ultrasonic arrays transmitting ultrasonic waves are switched by the drive array switching unit, and the processing described above is executed on the ultrasonic arrays. When a reflection position reflected by the object to be detected is detected at two points, the position calculating unit calculates the direction of the line connecting the two points and recognizes this as the position of the object to be detected.

In this measuring device, as mentioned above, it is simple to calculate and determine the position and axial direction of an object to be detected from ultrasonic wave reflection positions at two points on the object to be detected by the ultrasonic sensor.

A measurement system according to another aspect of the present invention includes the ultrasonic sensor described above.

As mentioned above, the ultrasonic sensor is able to detect the position of an object to be detected using a simple configuration which reduces manufacturing costs. The manufacturing costs of a measurement system using this ultrasonic sensor can also be reduced.

The measurement system as described above preferably further includes a control device connected to the ultrasonic sensor to communicate with the ultrasonic sensor, wherein the ultrasonic sensor is configured and arranged to transmit to the control device reception signals based on reflected ultrasonic waves detected by the ultrasonic arrays, and to drive the ultrasonic arrays based on drive signals inputted from the control device, and the control device includes a reflection position calculating unit configured to calculate a reflection position at which the ultrasonic waves are reflected based on the reception signals transmitted from the ultrasonic sensor, and a position calculating unit configured to calculate a position of an object to be detected from the reflection position detected by the reflection position calculating unit.

Here, signal communication between the ultrasonic sensor and the control device can be performed using a wired connection such as a lead wire, or using wireless communication via infrared, radio or BLUETOOTH®.

In this measurement system, as in the measurement device described above, the position and axial direction of an object to be detected can be easily calculated and determined from the ultrasonic wave reflection positions at two points on the object to be detected by the ultrasonic sensor.

Because various types of signal processing are performed by the control device, various types of calculation circuits do not have to be disposed in the ultrasonic sensor, and the size and thickness of the ultrasonic sensor can be reduced. This increases the versatility of the system. For example, when the position of a blood vessel inside the body is to be determined using this configuration, the probe can be attached to the body using tape.

BRIEF DESCRIPTION OF THE DRAWINGS

Referring now to the attached drawings which form a part of this original disclosure:

FIGS. 1A and 1B are perspective views showing an outline of the biological testing device in the first embodiment of the present invention in which FIG. 1A is a view from the obverse side of the biological testing device, and FIG. 1B is a view from the reverse side of the biological testing device;

DETAILED DESCRIPTION OF EXEMPLARY EMBODIMENTS

First Embodiment

The following is a description made with reference to the drawings of a biological testing device or measuring device equipped with the ultrasonic sensor in the first embodiment of the present invention.

1. Overall Configuration of Biological Testing Device

Figure 1A:
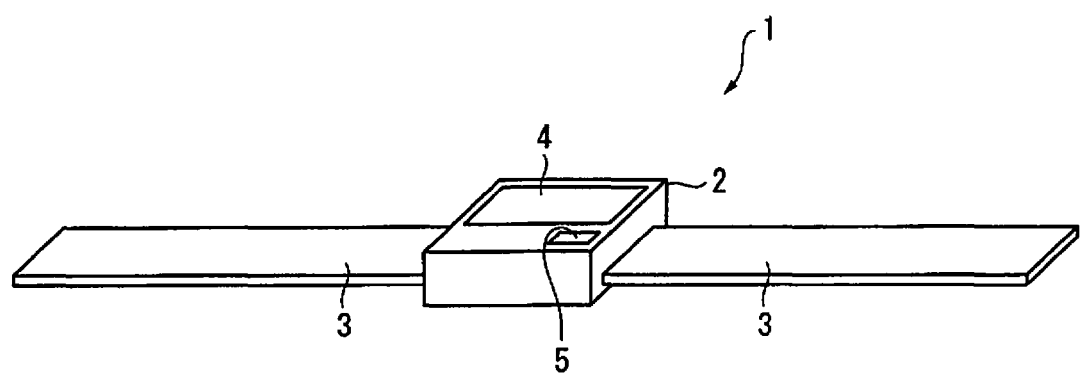
Figure 1B:
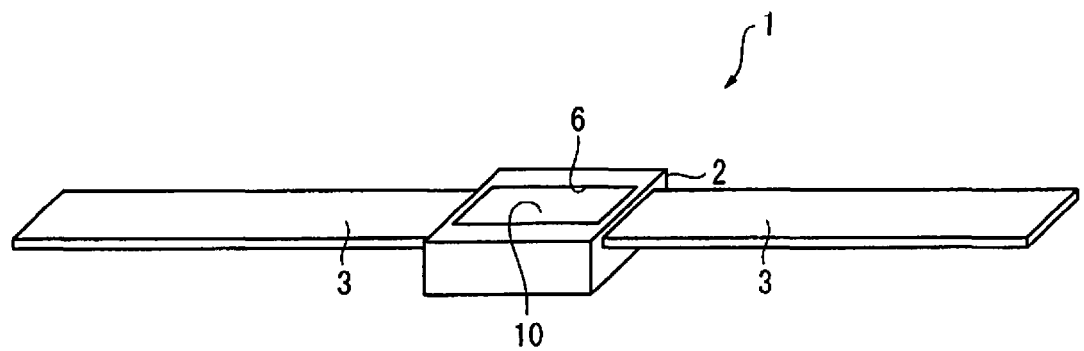

FIGS. 1A and 1B are perspective views showing an outline of the biological testing device in the first embodiment in which FIG. 1A is a view from the obverse side of the biological testing device, and FIG. 1B is a view from the reverse side of the biological testing device.

In FIG. 1, the biological testing device 1 measures the conditions in a blood vessel such as the blood flow, blood pressure and pulse using ultrasound. More specifically, as shown in FIG. 1, the biological testing device 1 has a device main unit 2 and a band 3 connected to the device main unit 2. The reverse side of this biological testing device 1 pressed against the body and fastened using the band 3, for example, to monitor and measure the conditions in a blood vessel over 24 hours.

2. Configuration of Device Main Unit

As shown in FIG. 1A, a display unit 4 for displaying measurement results and an operating unit 5 for operating the biological testing device 1 are disposed on the obverse side of the device main unit 2 of the biological testing device 1. A probe window 6 is formed in the reverse side of the device main unit 2, and a probe 10 equipped with an ultrasonic sensor of the present invention is disposed in the probe window 6. This probe 10 is attached to the body when blood vessel conditions inside the body are to be measured using the biological testing device 1.

Figure 2:
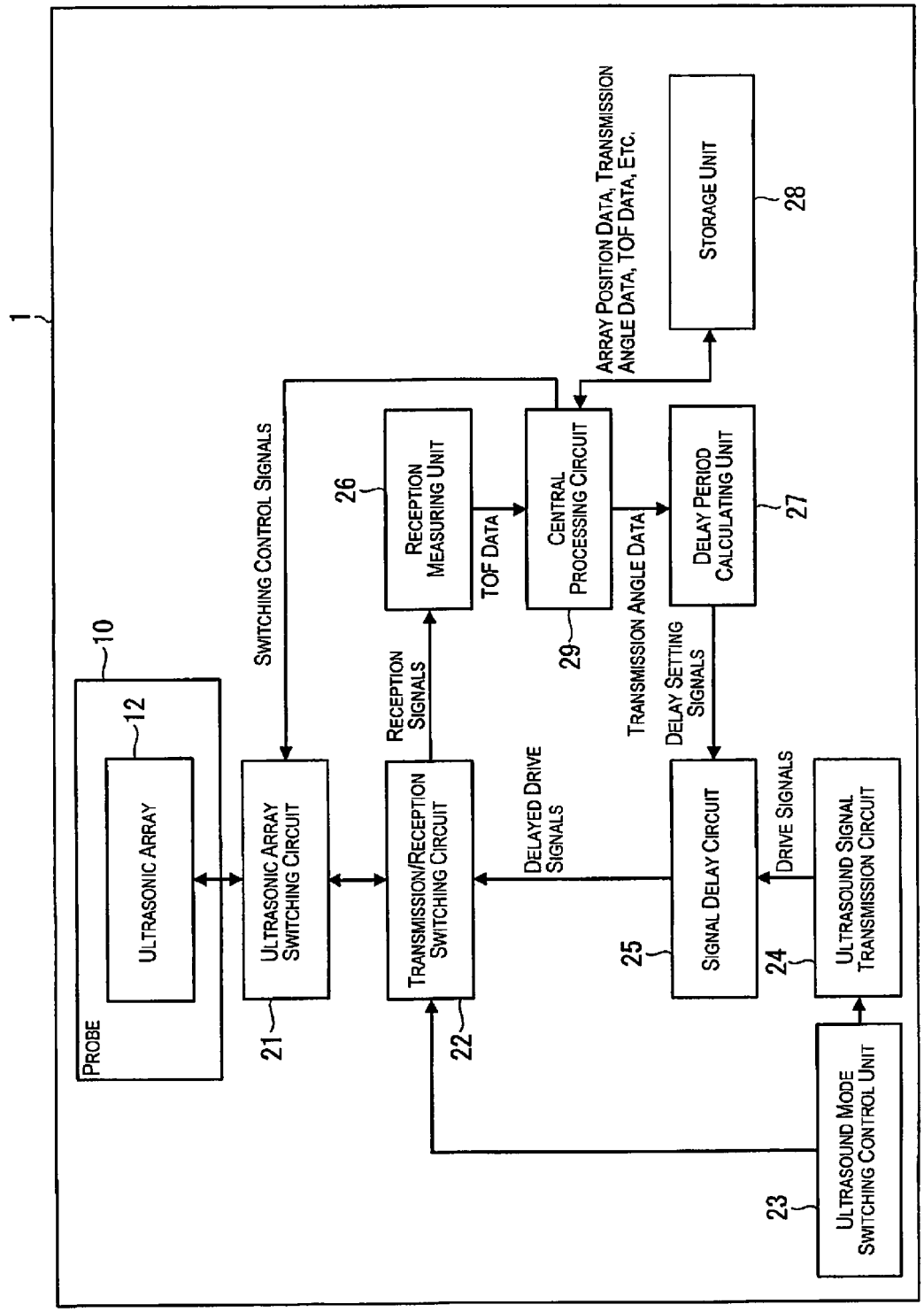
FIG. 2 is a block diagram showing a simplified configuration of the biological testing device in the first embodiment.

FIG. 2 is a block diagram showing a simplified configuration of the biological testing device 1 in the first embodiment.

As shown in FIG. 2, the biological testing device 1 has a probe 10, ultrasonic wave array switching circuit 21, transmission/reception switching circuit 22, ultrasound mode switching control unit 23, ultrasound signal transmission circuit 24, signal delay circuit 25, reception measuring unit 26, delay period calculating unit 27, storage unit 28, and central processing circuit 29. The ultrasonic sensor of the present invention includes the probe 10, the ultrasound signal transmission circuit 24, and the signal delay circuit 25.

2-1. Configuration of Probe

Figure 3:
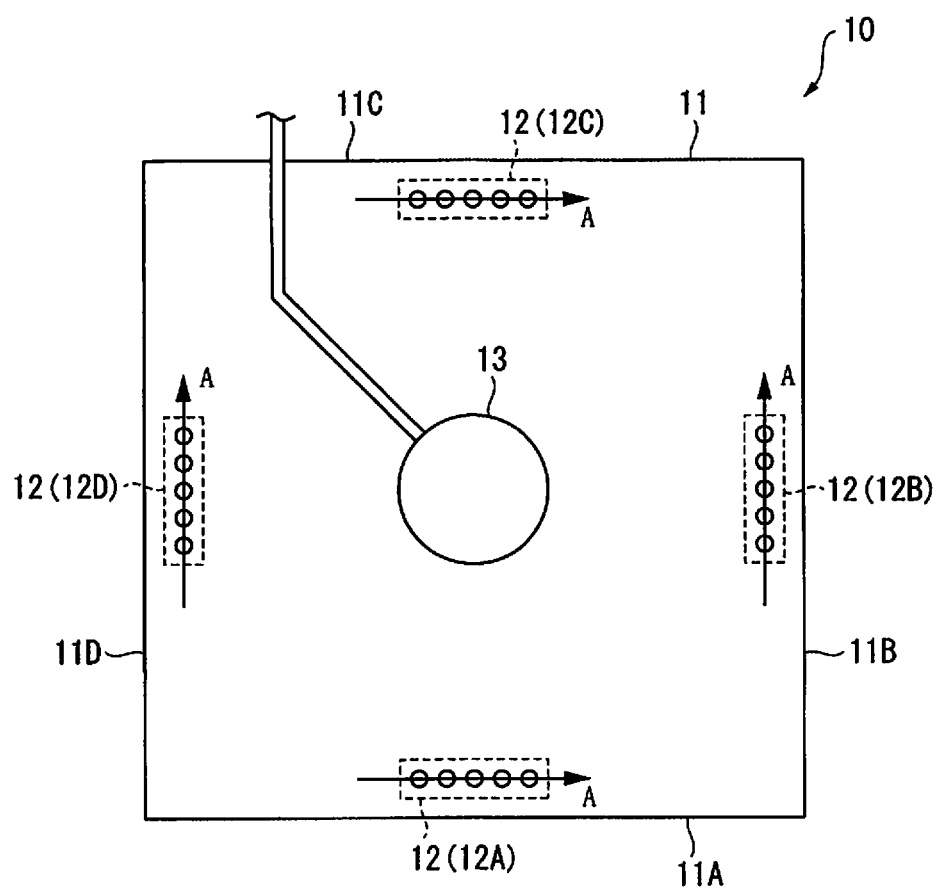
FIG. 3 is a top view showing a simplified configuration of the probe in the first embodiment.

FIG. 3 is a top view showing a simplified configuration of the probe in the first embodiment.

As shown in FIG. 3, the probe 10 has a rectangular substrate 11 constituting the probe surface of the present invention. Ultrasonic arrays 12 (12A, 12B, 12C, 12D) are disposed in the central portion of each side of the substrate 11 in plan view in which the substrate 11 is viewed from the thickness direction of the substrate 11. The biological testing sensor 13 for measuring the blood vessel conditions such as blood flow, blood pressure, and pulse is disposed in the planar central position of the substrate 11. More specifically, the probe 10 has a substrate 11, a support film 14 laminated on top of the substrate 11 (see FIGS. 4A and 4B), and a protective layer (not shown) covering the support film 14. The protective layer protects the ultrasonic array 12, biological testing sensor 13, and the wiring pattern formed on top of the support film 14 described below from external pressure. It is formed from a material with acoustic impedance similar to the human body, such as silicone rubber.

Figure 4A:
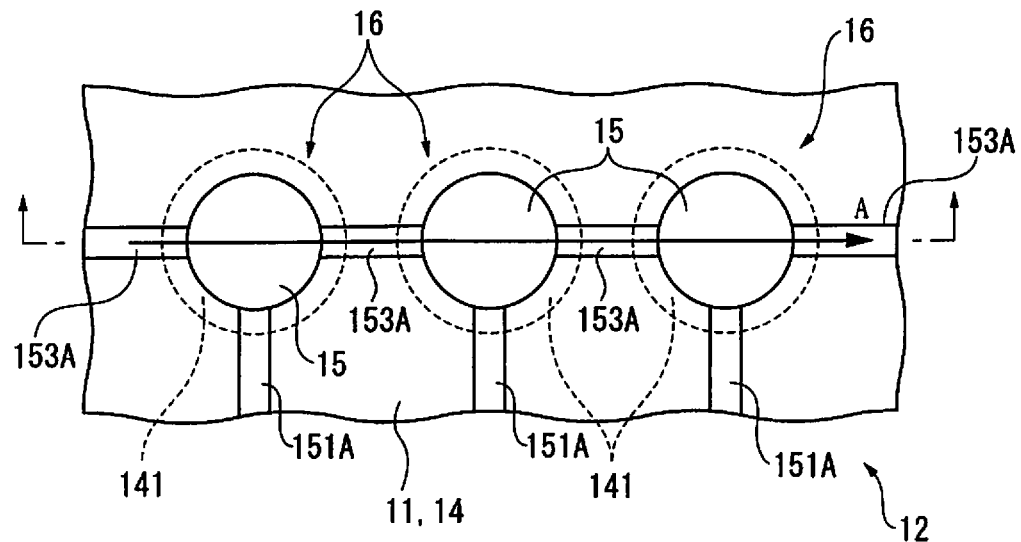
FIG. 4A is an enlarged top view and FIG. 4B is a cross-sectional view of the ultrasonic array in the first embodiment.
Figure 4B:
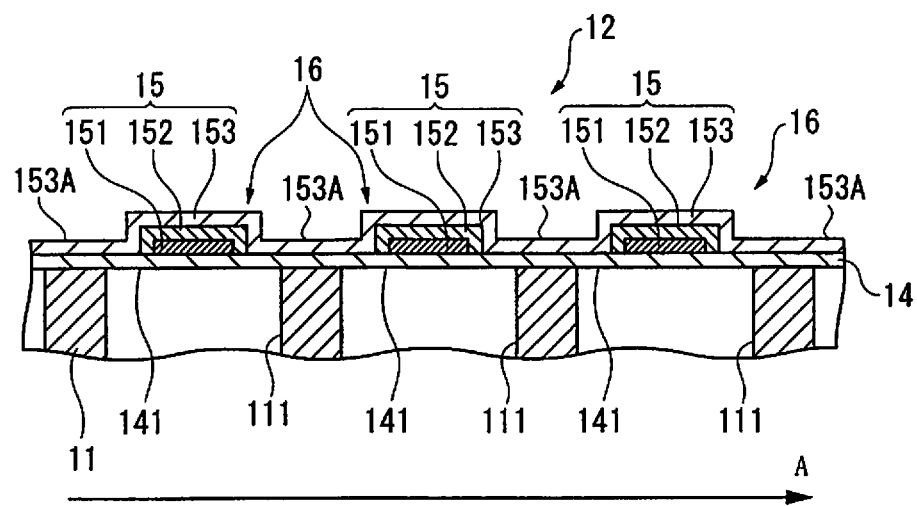

FIG. 4A is an enlarged top view and FIG. 4B is a cross-sectional view of the ultrasonic array. In FIGS. 4A and 4B, the protective layer has been removed.

As mentioned above, an ultrasonic array 12 is arranged in the central portion of each side of the substrate 11, and the ultrasonic array 12 includes an ultrasonic transducer 16 having a diaphragm 141 and a piezoelectric body 15.

Specifically, as shown in FIG. 4B, the substrate 11 has a plurality of openings 111 arranged in a straight line (linear scanning direction A) on each side (11A-11D). Also, a support film 14 is laminated on the substrate 11 as mentioned above, and the support film 14 blocks the openings 111.

The areas in which the openings 111 are blocked with the support film 14 constitute the diaphragms 141. A piezoelectric body 15 is disposed on top of the diaphragms 141.

Here, the direction in which the openings 111 are lined up, or the direction in which the ultrasonic transducers 16 are lined up, matches the linear direction of the sides 11A-11D. This is linear scanning direction A in the present invention. In other words, the ultrasonic array 12 has a linear array structure (one-dimensional array configuration) in which a plurality of ultrasonic transducers 16 are arranged in the linear scanning direction A. Here, in the first embodiment, each one of the ultrasonic transducers 16 constitutes an ultrasonic element of the present invention, and an ultrasonic array 12 is an element group in which a plurality of ultrasonic transducers 16 or ultrasonic elements is arranged in a one-dimensional array configuration.

In this embodiment, the probe 10 and the ultrasonic array 12 share the same substrate 11. However, the array substrate constituting the ultrasonic array 12 can be arranged separately on top of the substrate 11 constituting the probe 10.

The following is a more detailed explanation of a probe 10 and an ultrasonic transducer 16 in the present invention. The substrate 11 is formed from a semiconductor-forming material such as silicon (Si) which is easy to fashion using, for example, etching. The openings 111 formed in the substrate 11 are, for example, round in plan view. The planar shape of the openings is round in this explanation, but the present invention is not limited to this example. The openings can be formed in any shape such as a rectangle based on the deflection balance of the diaphragm 141 and the oscillation stability of the diaphragm 141 relative to the piezoelectric body 15.

The support film 14 is formed on top of the substrate 11 so as to block the openings 111. The support film 14 can have a two-layer configuration such as $SiO_2$ film and $ZrO_2$ film. Here, the $SiO_2$ film can be formed on the substrate surface using the thermal oxidation process when the substrate 11 is an Si substrate. The $ZrO_2$ film can be formed on top of the $SiO_2$ film using sputtering. Here, the $ZrO_2$ film prevents the spread of the Pb constituting the PZT in the $SiO_2$ film when PZT is used as the piezoelectric film 152 described below. Also, the $ZrO_2$ film has the effect of improving the deflection efficiency with respect to the distortion of the piezoelectric film 152.

The piezoelectric body 15 has a lower electrode 151 laminated on the upper layer of the support film 14, a piezoelectric film 152 formed on top of the lower electrode 151, and an upper electrode 153 formed on top of the piezoelectric film 152.

As shown, for example, in FIG. 4A, the lower electrode 151 is connected to a lower electrode wire 151A extending over the support film 14 in the perpendicular scanning direction perpendicular to the linear scanning direction A. This lower electrode wire 151A is disposed individually for the various ultrasonic transducers 16.

The upper electrode 153 is connected to an upper electrode wire 153A extending over the support film 14 in the linear scanning direction A. The upper electrode wire 153A is a shaped electrode wire in a single ultrasonic array 12. In other words, as shown in FIGS. 4A and 4B, the upper electrode wire 153A is connected to the upper electrode 153 of the adjacent ultrasonic transducer 16, and the end is connected, for example, to a GND. In this way, the upper electrode 153 of each ultrasonic transducer 16 is grounded.

Here, the upper electrode wire 153A is connected as a shared electrode wire for the ultrasonic array 12 to a GND, and the lower electrode wires 151A are formed independently. This allows the ultrasonic transducers 16 in this configuration to be operated individually. However, in another configuration, the lower electrode wire 151A can be connected as a shared electrode wire to a GND, and the upper electrode wires 153 can be formed individually.

The material used to form the lower electrode 151, the upper electrode 153, the lower electrode wire 151A, and the upper electrode wire 153A can be a conductive metal or a laminate composed of a plurality metal film layers. In this embodiment, the lower electrode 151 and the lower electrode wire 151A are made of a Ti/Ir/Pt/Ti laminate film, and the upper electrode 153 and the upper electrode wire 153A are made of Ir film.

The piezoelectric film 152 can be formed as PZT (lead zirconate titanate) film. In this embodiment, PZT is used as the piezoelectric film 152. However, other materials can be used as long as the film is able to shrink in the planar direction when voltage is applied. Examples of such materials include lead titanate ($PbTiO_3$), lead zirconate ($PbZrO_3$), and lead lanthanum titanate ($(Pb, La) TiO_3$).

In this type of ultrasonic transducer 16, the piezoelectric film 152 expands and shrinks in the planar direction when voltage is applied to the lower electrode 151 and the upper electrode 153. At this time, one surface of the piezoelectric film 152 is joined to the support film 14 via the lower electrode 151, and the upper electrode 153 is formed on the other surface. However, since another layer is not formed on top of the upper electrode 153, the support film 14 side of the piezoelectric film 152 is less likely to expand and shrink, while the upper electrode side 153 is more likely to expand and shrink. Thus, when a voltage is applied to the piezoelectric film 152, deflection occurs in which there is a protrusion on the opening 111 side, and the diaphragm 141 is deflected. As a result, when alternating current voltage is applied to the piezoelectric film 152, the diaphragm 141 vibrates in the film thickness direction, and the vibration of the diaphragm 141 transmits ultrasonic waves.

Also, when ultrasonic waves are received by an ultrasonic transducer 16 and the ultrasonic waves are inputted to the diaphragm 141, the diaphragm 141 vibrates in the film thickness direction. In an ultrasonic transducer 16, a potential difference occurs between the surface of the piezoelectric film 152 on the lower electrode 151 side and the surface on the upper electrode 153 side due to the vibration of the diaphragm 141. Reception signals (electric current) corresponding to the amount of displacement of the piezoelectric film 152 from the upper electrode 153 and the lower electrode 151 are then outputted.

In an ultrasonic array 12 in which a plurality of these ultrasonic transducers 16 is arranged in the linear scanning direction A, plane waves of these ultrasonic waves can be transmitted in the desired direction by delaying and staggering the timing for transmitting ultrasonic waves from the ultrasonic transducers 16.

Figure 5:
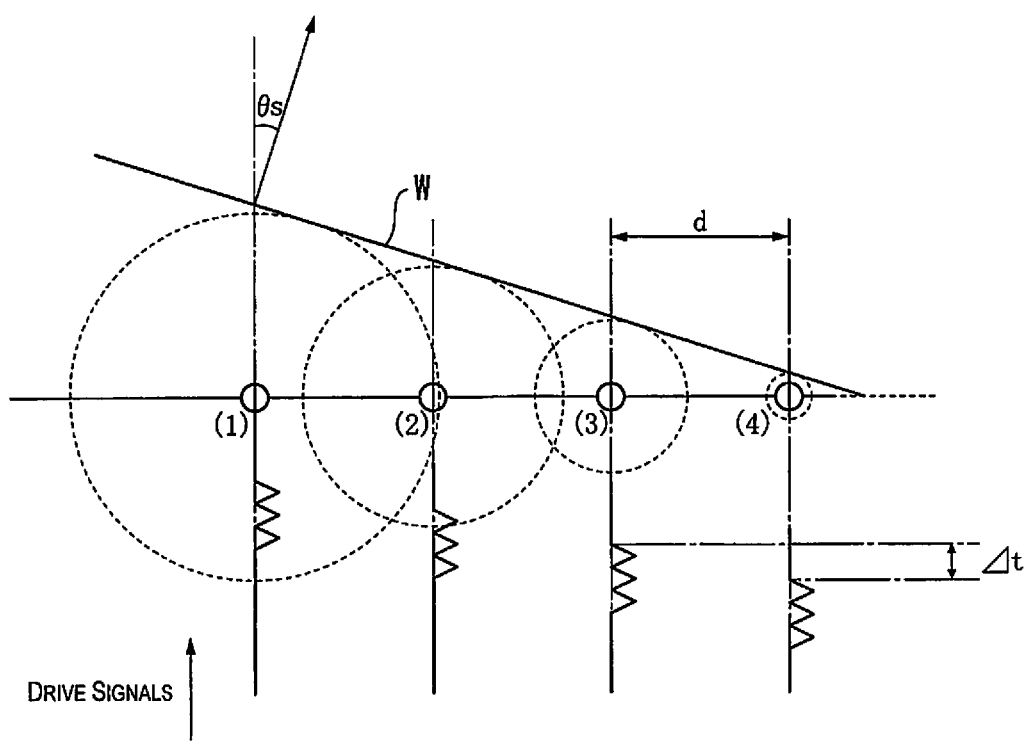
FIG. 5 is a view showing the transmission angle for the ultrasonic waves when the drive signals inputted to the ultrasonic elements (1)-(4) were delayed $\Delta t$ and then inputted.

FIG. 5 is a view showing the transmission direction (transmission angle) for the ultrasonic waves when the drive signals inputted to the ultrasonic elements (1)-(4) were delayed Δt and then inputted.

When the ultrasonic waves are transmitted from the ultrasonic transducers 16, the ultrasonic waves reinforce each other and are propagated as a synthesized wave front W.

Here, as shown in FIG. 5, when the drive signals inputted to the ultrasonic elements (1)-(4) set at an arranged distance d are delayed by Δt, the wave front of the ultrasonic waves transmitted from the ultrasonic transducers 16 to which drive signals had been inputted earlier and the wave front transmitted from the ultrasonic transducers 16 to which drive signals had been inputted later have a different phase. As a result, the synthesized wave front W is propagated at an angle to the linear scanning direction A.

When the transmission angle created by the propagation direction of the synthetic wave front W and the perpendicular scanning direction perpendicular to the linear scanning direction A at this time is θs and the speed of sound is c, the relationship in Equation (1) below is established.

Equation (1)

$$\Delta t = \frac{d \sin \theta_s}{c} \quad (1)$$

Figure 6:
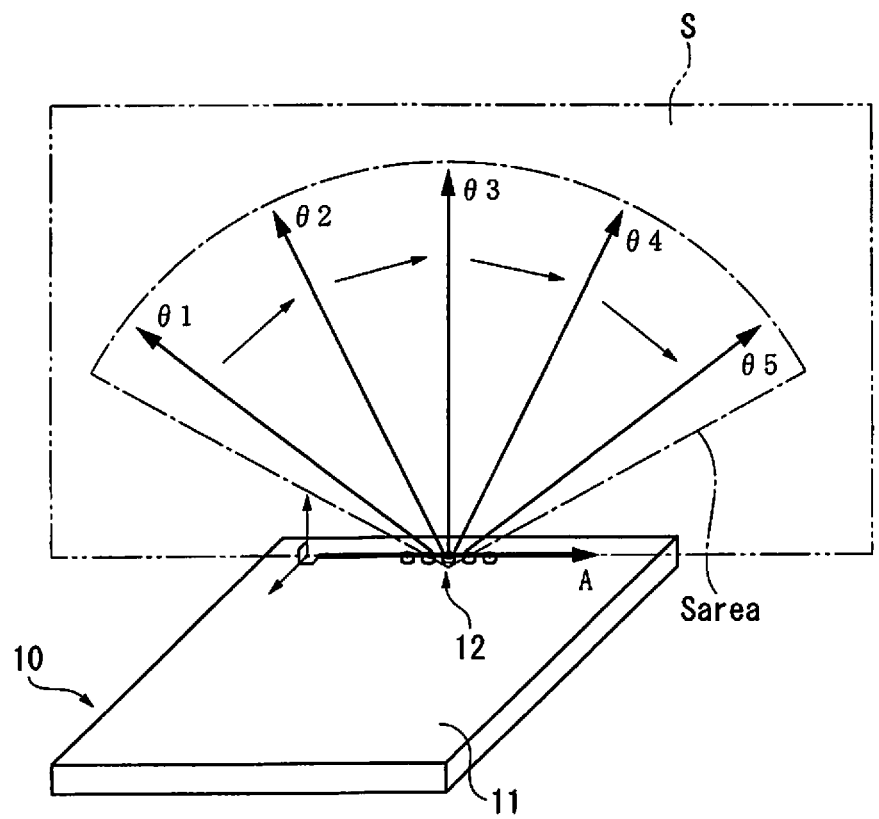
FIG. 6 is a view showing the scan area of the ultrasonic array in the first embodiment.
Figure 7:
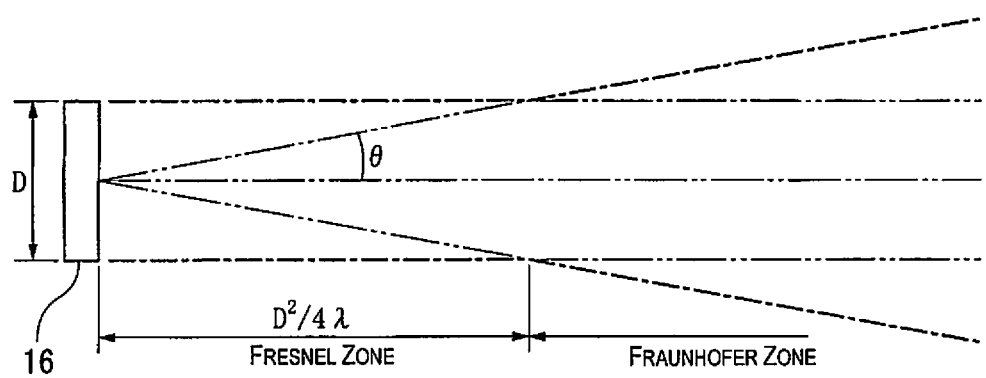
FIG. 7 is a view showing the ultrasound beam shape transmitted by the ultrasonic transducer in the first embodiment.

FIG. 6 is a view showing a scan area in which the position of a blood vessel can be measured using a single ultrasonic array 12, and FIG. 7 is a view showing the ultrasound beam shape transmitted by an ultrasonic transducer 16.

In the ultrasonic array 12, as mentioned above, the transmission angle of the ultrasonic waves can be changed by delaying the timing for the drive signals inputted to the ultrasonic transducers 16. Here, because the ultrasonic array 12 has a one-dimensional array configuration, the transmission angle of the ultrasonic waves, as shown in FIG. 6, are limited to passing in the linear scanning direction A within the plane (scanning plane S) perpendicular to the substrate 11. The transmission angle cannot be changed in the direction perpendicular to the scanning plane S.

Also, the ultrasonic waves transmitted from the diaphragms 141 of the ultrasonic transducers 16 having a limited area form the beam shape shown in FIG. 7 (as indicated by the dashed lines in FIG. 7). When the diameter of a diaphragm 141 of an ultrasonic transducer 16 is D and ultrasonic waves are generated with wavelength $\lambda$, the distance from the diaphragm 141 to $D^2/4\lambda$ is the Fresnel zone. In the Fresnel zone, the ultrasonic waves can be propagated substantially as plane waves. In the Fraunhofer zone, which is the zone beyond the Fresnel zone, the wave front of the ultrasonic waves is spherical and propagates through diffusion. Because the ultrasonic waves become diffused in the Fraunhofer zone, accurate position data cannot be obtained. Therefore, blood vessels in the Fraunhofer zone are not detected using ultrasound.

As mentioned above and shown in FIG. 6, the scan area S able to measure the position of a blood vessel from a single ultrasonic array 12 is a fan-shaped area passing in the linear scanning direction A within a scan plane S perpendicular to the substrate 11, and remaining within the Fresnel zone from the ultrasonic array 12 (i.e., a range in which the distance from the ultrasonic array 12 is $D2/4\lambda$).

Because the thickness dimension of the ultrasonic transducer 16 is sufficiently small in the perpendicular scanning direction, the scan area Sarea of the ultrasonic array 12 is within the scan plane S. However, when the ultrasonic transducer 16 is formed lengthwise in the perpendicular scanning direction, the scan area Sarea is a volume area having a width area which is simply the dimension of the ultrasonic transducer 16 in the longitudinal direction.

In the probe 10 of this embodiment, the ultrasonic arrays 12 described above are arranged in the central portions of each side 11A-11D of the substrate 11. As a result, a closed area is formed which is surrounded by the linear scanning directions A of four ultrasonic arrays 12. The scan area Sarea of each ultrasonic array 12 extends in the linear scanning directions A and is formed within a scan plane S perpendicular to the substrate 11. Therefore, the sides Sa, Sb, Sc, Sd of the rectangular area directly below the probe 10 (see FIG. 9: referred to as the underside area Sv) overlap with the scan area Sarea of each ultrasonic array. In this probe 10, when a blood vessel passes through the underside area Sv of the probe 10, the blood vessel intersects two of the four sides Sa, Sb, Sc, Sd. Therefore, the points at which the blood vessel intersects the sides Sa, Sb, Sc, Sd can be detected by transmitting ultrasonic waves into the scan area Sarea from the ultrasonic arrays 12, and receiving the reflected ultrasonic waves.

2-2. Configuration of Ultrasonic Array Switching Circuit

Returning to FIG. 2, the following is an explanation of another configuration of the device main unit 2.

The ultrasonic array switching circuit 21 is a switching circuit for switching the operated ultrasonic array 12 among the four ultrasonic arrays 12 disposed on the probe 10.

In the biological testing device 1 in this embodiment, while one ultrasonic array 12 is sending and receiving ultrasonic waves, a drive signal is outputted to the other ultrasonic arrays 12, and reception signals cannot be received from the other ultrasonic arrays 12. In this way, the activated ultrasonic array 12 receives ultrasonic waves from the other ultrasonic arrays 12, and problems are avoided such as the detection of noise and the detection of reception signals by the non-activated ultrasonic arrays 12.

This ultrasonic array switching circuit 21 can have a terminal group connected to the upper electrode wires 153A and the lower electrode wires 151A of the various ultrasonic arrays 12. The terminal group corresponding to the ultrasonic array 12 receiving a switching control signal is connected to the transmission/reception switching circuit 22 based on the switching control signals from the central processing circuit 29 for selecting the inputted array. The terminal groups corresponding to the non-activated ultrasonic arrays 12, for example, connect the lower electrode wires 151A and the upper electrode wires 153A to the GND so that they are not activated.

2-3. Configuration of Transmission/Reception Switching Circuit

The transmission/reception switching circuit 22 is a switching circuit for switching the connection mode based on mode switching signals inputted from the ultrasound mode switching control unit 23.

More specifically, when control signals to switch to the ultrasound transmission mode are inputted from the ultrasound mode switching control unit 23, the transmission/reception switching circuit 22 switches to a connection mode allowing the drive signals inputted from the signal delay circuit 25 to be outputted to the ultrasonic array switching circuit 21. When control signals are inputted from the ultrasound mode control unit 23 for switching to the ultrasound reception mode, the transmission/reception switching circuit 22 switches to a connection mode allowing the reception signals inputted from the ultrasonic array switching circuit 21 to be outputted to the reception measuring unit 26.

2-4. Configuration of Ultrasound Mode Switching Control Unit

The ultrasound mode switching control unit 23 switches between the ultrasound transmission mode in which ultrasonic waves are transmitted from an ultrasonic array 12 and the ultrasound reception mode in which ultrasonic waves are received by an ultrasonic array 12.

More specifically, when control signals for initiating a blood vessel position measurement are inputted from the central processing circuit, the ultrasound mode switching control unit 23 first executes the process for switching to an ultrasound mode. In this process, the ultrasound mode switching control unit 23 outputs controls signals to the transmission/reception switching circuit 22 for switching to the transmission mode, and outputs control signals for outputting drive signals from the ultrasound signal transmission circuit 24. Also, the ultrasound mode switching control unit 23 executes a process in which the time measured by a timing unit (timer) not shown in the drawings is determined, and a switch from the ultrasound transmission mode to the ultrasound reception mode is effected after a predetermined transmission time period has elapsed. The transmission time period is set based on the amount of time, for example, in which one or two frequency bursts are transmitted from an ultrasonic array 12. In the reception mode, the ultrasound mode switching control unit 23 outputs control signals to the transmission/reception switching circuit 22 for switching to the reception mode, and the transmission/reception switching circuit 22 is switched to a connection mode in which reception signals inputted from the ultrasonic array 12 can be inputted to the reception measuring unit 26.

The ultrasound mode switching control unit 23 performs this process a predetermined number of times. This number of times is set based on the number of ultrasonic wave transmission angle settings. For example, as shown in FIG. 6, the process can be repeated five or more times when the blood vessel position is measured by switching the ultrasonic wave transmission angle in five stages.

The process can also be repeated based on the reception signals when a blood vessel position cannot be detected.

2-5. Configuration of Ultrasound Signal Transmission Circuit

When control signals are inputted during the transmission mode to output control signals from the ultrasound mode switching control unit 23, the ultrasound signal transmission circuit 24 outputs drive signals (drive voltage) for driving the ultrasonic transducers 16 in the ultrasonic array 12 to the signal delay circuit 25.

2-6. Configuration of Signal Delay Circuit

When drive signals are inputted from the ultrasound signal transmission circuit 24 to the ultrasonic transducers 16, the signal delay circuit 25 delays the drive signals and outputs them to the transmission/reception switching circuit 22.

Here, the signal delay circuit 25 delays each drive signal for driving the ultrasonic transducers 16 by $\Delta t$ and outputs them to the transmission/reception switching circuit 22 based on the delay setting signals inputted from the delay period calculating unit 27.

2-7. Configuration of Reception Measuring Unit

The reception measuring unit 26 monitors the time measured by the timing unit and measures the period of time until ultrasonic waves are received.

More specifically, the reception measuring unit 26 monitors the timing for the process in which the ultrasound mode switching control unit 23 switches to the transmission mode. In other words, it monitors the time from which ultrasonic waves are transmitted from the ultrasonic array 12 to which the count on the timing unit is reset by the ultrasound mode switching control unit 23. When the ultrasound mode switching control unit 23 switches to the reception mode and reception signals corresponding to the reflected ultrasonic waves received by an ultrasonic array 12 are inputted from the transmission/reception switching circuit 22 to the reception measuring unit 26, the time (TOF data: time-of-flight data) is obtained for the inputted timing. The TOF data thus obtained is inputted to the central processing circuit 29.

2-8. Configuration of Delay Period Calculating Unit

The delay period calculating unit 27 calculates the drive delay period for the ultrasonic transducers 16 based on the transmission angle data inputted from the central processing circuit 29.

Here, the transmission angle data is stored beforehand in the storage unit 28. For example, in this embodiment, as shown in FIG. 6, five transmission angle data sets $\theta s = \theta 1 - \theta 5$ are stored beforehand. However, six or more transmission angle data sets can be stored to change the transmission angle in finer increments.

The delay period calculating unit 27 calculates the delay period $\Delta t$ based on Equation (1) using the inputted transmission angle data $\theta s$, the preset element pitch d for the ultrasonic transducers 16, and the speed of sound c. It then outputs the result as delay setting signals to the signal delay circuit 25.

2-9. Configuration of Storage Unit

The storage unit 28 stores the various types of programs and the various types of data used to execute the various types of processes performed by central processing circuit 29 and the delay period calculating unit 27.

More specifically, the various types of data include the position data for the ultrasonic arrays 12 in the probe 10, the transmission angle data $\theta s$, and the TOF data. Also, the various types of programs include the control programs for controlling all of the blood vessel measurement processes, the reflection position calculating programs for calculating the coordinate position for one point of a blood vessel based on the TOF data, and the blood vessel position measurement program for calculating the position of a blood vessel from the reflection position at two points.

2-10. Configuration of Central Processing Circuit

The central processing circuit 29 executes various types of processes by expanding programs stored in the storage unit 28. Here, the central processing circuit 29 retrieves and executes a reflection position calculating program stored in the storage unit 28 to function as the reflection position calculating unit of the present invention, and retrieves and executes a blood vessel position measuring program stored in the storage unit 28 to function as the position calculating unit of the present invention. In other words, the central processing circuit 29 constitutes the reflection position calculating unit and position calculating unit of the present invention.

When, for example, the user operates the operating unit 5 to input signals for initiating a blood vessel position measurement, the central processing circuit 29 outputs control signals to the ultrasound mode switching control unit 23 to initiate a measurement. Also, the central processing circuit 29 outputs switching control signals to the ultrasound array switching circuit 21 to switch the ultrasonic arrays 12. In addition, the central processing circuit 29 retrieves the transmission angle data from the storage unit 28 and inputs this data to the delay period calculating unit 27. Also, the central processing circuit 29 executes the reflection position calculating process using the reflection position calculating program to calculate the position at which the ultrasonic waves are reflected. Then, the central processing circuit 29 executes the blood vessel position calculating process using the blood vessel position measurement program to calculate the position coordinates of the blood vessel and the axial direction of the blood vessel.

Also, the central processing circuit 29 tests the blood vessels conditions using the biological testing sensor 13 on the blood vessel identified by the blood vessel position calculating process, measures, for example, the blood flow, blood pressure and pulse, and displays the results on the display unit 4.

3. Blood Vessel Measurement Process for Biological Testing Device

Figure 8:
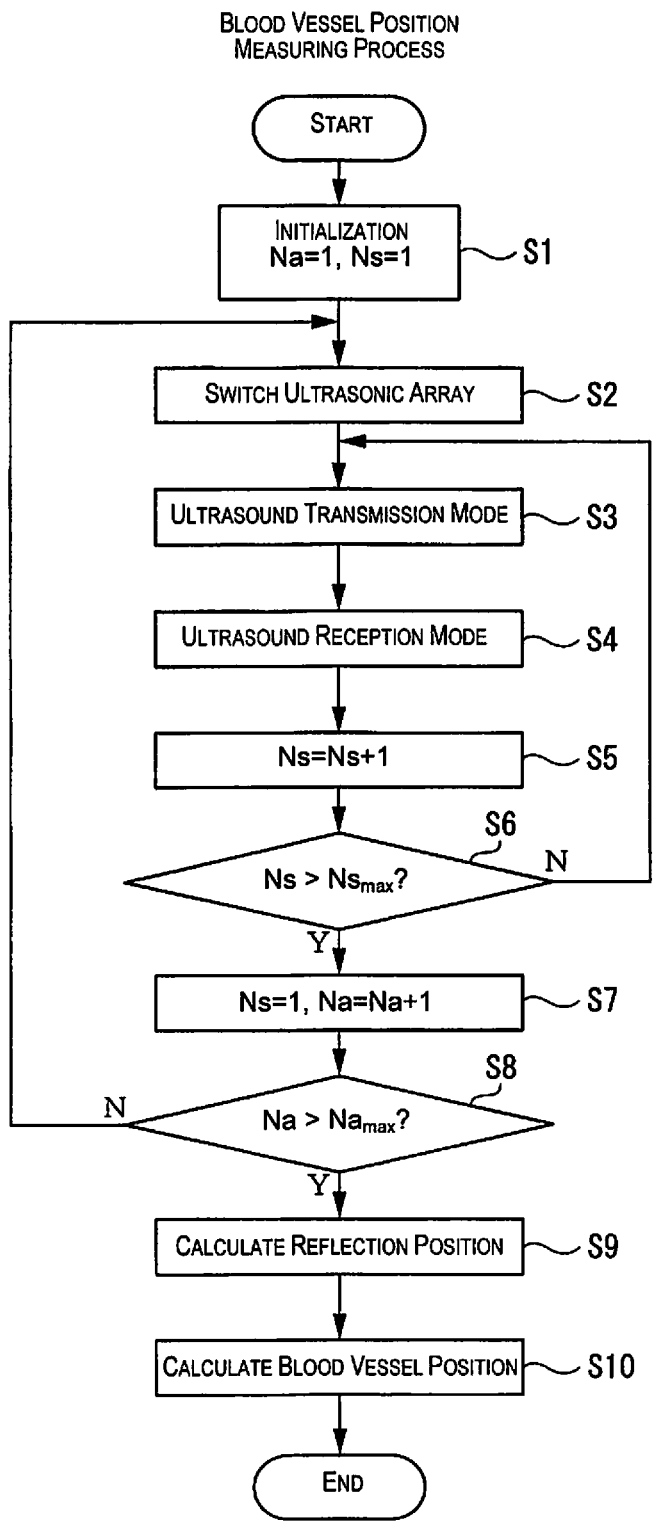
FIG. 8 is a flowchart of a blood vessel position measuring process performed by the biological testing device in the first embodiment.
Figure 9:
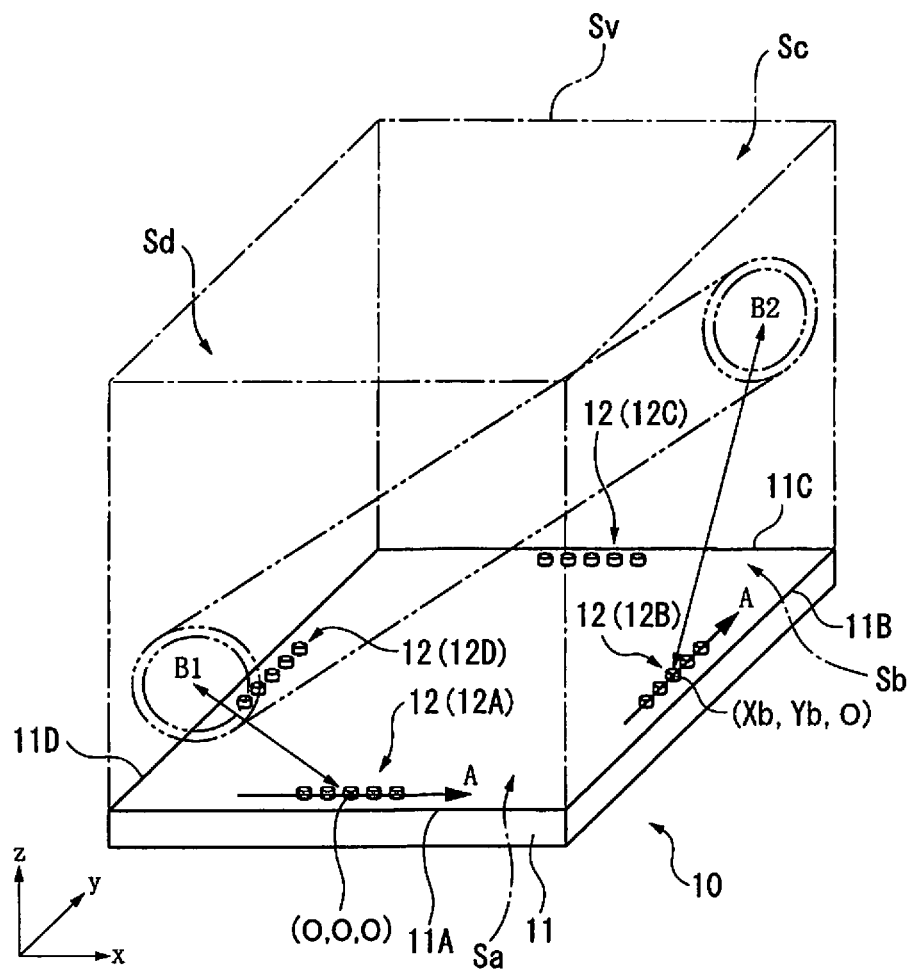
FIG. 9 is a schematic diagram showing an example in which a blood vessel is in the area directly below the probe.
Figure 10A:
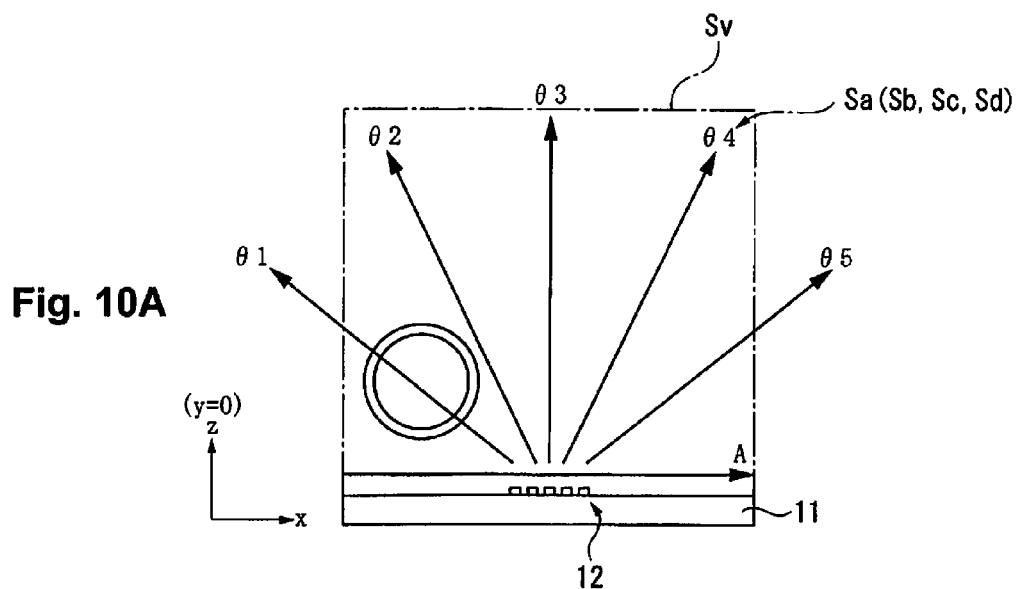
FIGS. 10A to 10C are diagrams used to explain the reflection position measurement method.

The following is an explanation with reference to the drawings of the blood vessel position measuring process performed by this biological testing device 1. FIG. 8 is a flowchart of the blood vessel position measuring process performed by the biological testing device. FIG. 9 is a schematic diagram showing an example in which a blood vessel is in the area directly below the probe. FIG. 10 is a diagram used to explain the reflection position measurement method.

As mentioned above, the probe 10 in the biological testing device 1 of this embodiment is placed on the part of the body to be tested such as an arm, and the device main unit 2 is fastened using the band 3 and secured to the position to be tested. In this way, the user does not have to hold the device main unit manually for a long period of time. This also allows blood vessel conditions to be measured readily over a long period of time.

When the user operates the operating unit 5 and inputs input signals, the biological testing device 1 begins to measure blood vessel conditions.

When conditions of a blood vessel are to be measured, the biological testing device 1 first measures the position of the blood vessel (blood vessel position measuring process), and then the blood vessel condition measurements such as blood pressure, blood flow and pulse are performed on the blood vessel at the measured blood vessel position.

The following is an explanation of the blood vessel position measurement process. In the blood vessel position measurement process, as shown in FIG. 8, the central processing circuit 29 in the biological testing device 1 first performs the initialization process (Step S1). In the initialization process, the array variable Na and the angle variable Ns are initialized. In other words, Na=1 and Ns=1 are set.

Next, the central processing circuit 29 executes the switching process allowing the ultrasonic array 12 with the array variable Na to be operated (Step S2). Here, the central processing circuit 29 outputs a switching control circuit to the ultrasonic array switching circuit 21 to switch to ultrasonic array 12A when the array variable Na is Na=1, outputs a switching control circuit to the ultrasonic array switching circuit 21 to switch to ultrasonic array 12B when the array variable Na is Na=2, outputs a switching control circuit to the ultrasonic array switching circuit 21 to switch to ultrasonic array 12C when the array variable Na is Na=3, and outputs a switching control circuit to the ultrasonic array switching circuit 21 to switch to ultrasonic array 12D when the array variable Na is Na=4.

Afterwards, the central processing circuit 29 performs various types of processes in the ultrasound transmission mode (Step S3).

In the ultrasound transmission mode, the central processing circuit 29 retrieves the transmission angle data θs from the storage unit 28 and outputs the data to the delay period calculating unit 27. Because the angle variable is Ns=1 after initialization has been performed in Step S1, the transmission angle data θ1 is retrieved and outputted to the delay period calculating unit 27. In this way, the delay period calculating unit 27 calculates the delay period Δt based on Equation (1), and outputs the result to the signal delay circuit 25 as delay setting signals.

Also, the central processing circuit 29 outputs control signals to the ultrasound mode switching control unit 23 to switch to the ultrasound transmission mode. When control signals have been inputted from the central processing circuit 29, the ultrasound mode switching control unit 23 outputs control signals to the transmission/reception switching circuit 22 to output the drive signals inputted from the signal delay circuit 25 to the ultrasonic array switching circuit 21. Also, the ultrasound mode switching control unit 23 outputs control signals to the ultrasound signal transmission circuit 24 to transmit drive signals for operating an ultrasonic array 12.

In this way, drive signals (drive pulses) are outputted to the signal delay circuit 25 from the ultrasound signal transmission circuit 24 to be outputted to the ultrasonic transducers 16 of the ultrasonic array 12. Also, the signal delay circuit 25 inputs delay setting signals from the delay period calculating unit 27 as mentioned above. As a result, the various drive signals are delayed by a delay period based on the delay setting signal and then outputted to the transmission/reception switching circuit 22.

Also, the transmission/reception switching circuit 22, as mentioned above, is switched by the control signals inputted from the ultrasound mode switching control unit 23 to a mode enabling the output of the drive signals inputted from the signal delay circuit 25 to the ultrasonic array switching circuit. As a result, the drive signals from the delay processing outputted from the signal delay circuit 25 are outputted to the ultrasonic transducers 16 in the ultrasonic array 12 corresponding to the array variable Na.

As explained above, ultrasonic waves are then outputted from the ultrasonic array 12 corresponding to the array variable Na at the transmission angle corresponding to the angle variable Ns.

Also, the ultrasound mode switching control unit 23 receives control signals from the central processing circuit 29 for switching to the ultrasound transmission mode, and outputs drive signals from the ultrasound signal transmission circuit 24 at a certain timing. In other words, the time measured by the timing unit is reset and the time elapsed measured on the timing used to transmit ultrasonic waves from the ultrasonic array 12. The ultrasound mode switching control unit 23 then executes the various processes in the ultrasound reception mode after the time in which, for example, one or two frequency bursts have been outputted (Step S4).

The transmission end time for ending the output of ultrasound signals from the ultrasonic transducer 16 can be calculated by the ultrasound mode switching control unit 23 based on the delay period Δt calculated by the delay period calculating unit 27, and the switching control can be performed to the reception mode after the transmission end time has elapsed from the timing used to transmit ultrasonic waves from the ultrasonic array 12.

In the ultrasonic reception mode of Step S4, the ultrasound mode switching control unit 23 outputs to the transmission/reception switching circuit 22 control signals for outputting the reception signals inputted from the ultrasonic array switching circuit 21 to the reception measuring unit 26.

Thus, when ultrasonic waves are received by the ultrasonic array 12, and reception signals have been inputted from the ultrasonic array switching circuit 21 to the reception switching circuit 22, the reception signals are outputted to the reception measuring unit 26.

The reception measuring unit 26 monitors the time counted by the timing unit, obtains the TOF data, or the time from the timing used to transmit ultrasonic waves to the timing for inputting reception signals, and outputs this data to the central processing circuit 29. The central processing circuit 29 then appropriately stores the inputted TOF data in the storage unit 28 so as to be retrievable.

Figure 10B:
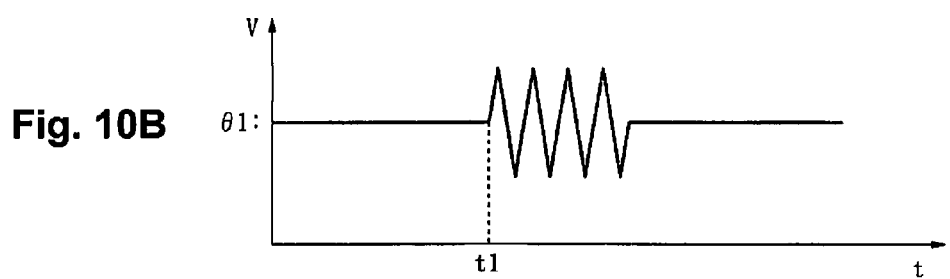
Figure 10C:
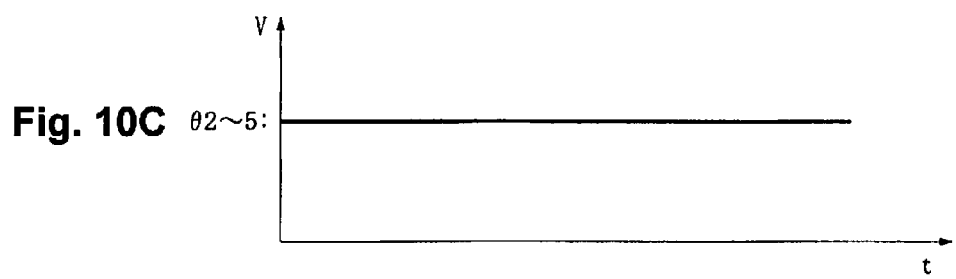

Here, when the ultrasonic waves transmitted from the ultrasonic array 12 are reflected by a blood vessel, reception signals are received as shown in FIG. 10B. However, the reception measuring unit 26 obtains time point t1 inputted by the reception signals as TOF data. In the example shown in FIG. 10, when ultrasonic waves are transmitted from the ultrasonic array 12 at transmission angles θ2-θ5, reflection waves cannot be detected, and the signal waveform shown in FIG. 10C is obtained. Because the reception measuring unit 26 cannot obtain TOF data when reflection waves are not detected, it does not execute the TOF data recording process in the storage unit 28.

Afterwards, the central processing circuit 29 adds 1 to the angle variable Ns (Step S5), and determines whether the angle variable Ns has reached the maximum value $Ns_{MAX}$ (Step S6). In this embodiment, $Ns_{MAX}$=5 because ultrasonic waves are transmitted from the ultrasonic array at angles in five stages. In Step S6, when Ns≤$Ns_{MAX}$ (Ns≤5 in this embodiment), the central processing circuit 29 returns to the ultrasound transmission mode in Step S3.

In Step S6, when Ns>$Ns_{MAX}$ (Ns>5 in this embodiment), the angle variable Ns is initialized, Ns=1 is set, and 1 is added to the array variable Na (Step S7).

The central processing circuit 29 then determines whether or not the array variable Na has exceeded the maximum value $Na_{MAX}$ (Step S8). In this embodiment, $Na_{Max}$=4 because there are four ultrasonic arrays 12 disposed on the probe 10.

When, in Step S8, the array variable Na is less than the $Na_{Max}$ (4 in this embodiment), the process returns to Step S2, and a scan is performed with another ultrasonic array 12.

When, in Step S8, the array variable Na is Na>$Na_{Max}$, the central processing circuit 29 retrieves the reflection position calculating program from the storage unit 28 and performs the reflection position calculating process (Step S9).

In the reflection position calculating process, the central processing circuit 29 identifies the reflection position at which ultrasonic waves were reflected based on Equations (2)-(3) below. In other words, when a blood vessel passes through the underside area Sv of the probe 10, as shown in FIG. 9, the blood vessel passes through the four sides 11A-11D of the substrate 11, and intersects at least two of the four sides Sa, Sb, Sc, Sd perpendicular to each side 11A-11D. Thus, the reflection position coordinates at two points of intersection can be determined from calculations using Equations (2) and (3) below.

Equations (2) and (3)

$$B1(X_1, 0, Z_1) = \left(c \cdot \frac{t_1}{2} \cdot \sin\theta_1, 0, c \cdot \frac{t_1}{2} \cdot \cos\theta_1\right) \quad (2)$$

$$B2(X_2, Y_2, Z_2) = \left(X_b, Y_b + c \cdot \frac{t_2}{2} \sin\theta_2, c \cdot \frac{t_2}{2} \cdot \cos\theta_2\right) \quad (3)$$

As shown in FIG. 9, Equation (2) is an equation indicating the reflection position in which ultrasonic array 12A is the origin point, ultrasonic waves are transmitted from the ultrasonic array 12A at transmission angle θ1, and the time (TOF) until reception signals are received is t1. Equation (3) is an equation indicating the reflection position in which ultrasonic waves are transmitted from the ultrasonic array 12B arranged at coordinate position (Xb, Yb, 0) at transmission angle θ2, and the TOF is t2. Here, as shown in FIG. 9, the blood vessel intersects the y=0 plane (side plane Sa) and the x=Xb plane (side plane Sb). As a result, the reflection positions detected by ultrasonic arrays 12C and 12D are omitted. Ultrasonic arrays 12C, 12D are disposed at positions targeted by ultrasonic arrays 12A, 12B with respect to the center point of the substrate 11, and their positions can be easily calculated using variations of Equations (2) and (3).

Afterwards, the central processing circuit 29 retrieves the blood vessel position measurement program from the storage unit 28 and executes the blood vessel position measuring process (Step S10).

In the blood vessel position measuring process, the underside area Sv of the probe 10 is sufficiently small that the position of the blood vessel is considered to run along a straight line connecting the two points of intersection B1, B2 calculated in Step S9. This is the measurement result for the blood vessel position.

When, for example, in FIG. 10, the blood vessel intersects the y=0 plane (side plane Sa) and the x=Xb plane (side plane Sb) in the underside area of the probe, the position coordinates for points of intersection B1 and B2 are calculated in Step S9 using Equations (2) and (3) above. Here, the straight line connecting the points of intersection B1, B2 can be determined using Equation (4) below.

In this way, the position of a blood vessel passing through the underside area of the probe 10 can be measured.

Equation (4)

$$\begin{pmatrix} x \\ y \\ z \end{pmatrix} = \begin{pmatrix} X_1 \\ 0 \\ Z_1 \end{pmatrix} + \frac{t}{\sqrt{(X_2 - X_1)^2 + Y_2^2 + (Z_2 - Z_1)^2}} \begin{pmatrix} X_2 - X_1 \\ Y_2 - 0 \\ Z_2 - Z_1 \end{pmatrix} \quad (4)$$

$$= \begin{pmatrix} X_1 \\ 0 \\ Z_1 \end{pmatrix} + \frac{t}{\sqrt{(X_b - X_1)^2 + Y_2^2 + (Z_2 - Z_1)^2}} \begin{pmatrix} X_b - X_1 \\ Y_2 \\ Z_2 - Z_1 \end{pmatrix}$$

Also, in the biological testing device 1, the process in Step S1 through Step S9 can be repeated periodically to obtain the change in the position of the blood vessel over a long period of time. The biological testing device 1 in this embodiment can remain attached to the user using the band 3, and measurements can be conducted periodically to accurately identify the position of the blood vessel even when the position of the blood vessel changes because of movement by the user. Thus, blood vessel conditions (blood flow, blood pressure, pulse, etc.) can be measured at the exact position of the blood vessel over a long period of time.

4. Operations and Effects of Biological Testing Device

As mentioned above, the biological testing device 1 in this embodiment has a substrate 11 constituting the probe surface, and a plurality of ultrasonic arrays 12 arranged on the substrate 11. The ultrasonic array 12 has a one-dimensional array configuration in which a plurality of ultrasonic transducers 16 is arranged in a linear scanning direction A. These ultrasonic arrays 12 are arranged in positions apart from one another and in different linear scanning directions A. The biological testing device 1 also has an ultrasound signal transmission circuit 24 and a signal delay circuit 25. In this configuration, the input timing for the drive signals inputted to the various ultrasonic transducers 16 is delayed by the ultrasound signal transmission circuit 24 and the signal delay circuit 25, and the ultrasonic wave transmission direction is changed to the desired transmission angle within the scan plane S.

In this biological testing device 1, the ultrasonic waves reflected off a blood vessel can be detected by at least two ultrasonic arrays 12, and two reflection positions of a blood vessel passing through the underside area Sv of the probe 10 can be determined. In this way, the direction of the blood vessel and the position of the blood vessel can be measured from the coordinates of the two reflection positions.

In this configuration, ultrasonic arrays 12 do not cover the entire substrate 11 of the probe 10. The areas of the substrate 11 in which ultrasonic arrays 12 are not arranged can be patterned with wiring for the biological testing sensor 13 or with wiring for the ultrasonic array 12. This simplifies the configuration. In other words, the wiring patterns connected to the ultrasonic elements are complicated when the substrate 11 is covered with ultrasonic arrays for measuring the position of a blood vessel or when an ultrasonic array is composed of a plurality of ultrasonic elements arranged in a two-dimensional array configuration. It can be difficult to form wiring patterns when biological testing sensors are arranged on the same substrate. For example, lead wires from outside of the substrate 11 have to be connected directly to a biological testing sensor. This increases the overall size of the ultrasonic sensor. In this embodiment, by contrast, ultrasonic arrays 12 in a one-dimensional configuration are disposed on top of a substrate 11 in positions apart from one another. Because this simplifies the wiring patterns, the ultrasonic sensors and biological testing devices 1 are not large. In fact, the devices are small enough to be readily attached to an arm or other body part.

Also, the ultrasonic arrays 12 described above are arranged in the central portion of each side 11A-11D of the substrate 11, and the linear scanning directions A of these ultrasonic arrays 12 are arranged in the directions of these sides 11A-11D. As a result, the probe 10 is surrounded by the linear scanning directions A in each of the ultrasonic arrays 12. Because in this configuration, the underside area Sv of the probe 10 is surrounded by the scan area Sarea of the ultrasonic arrays 12, a blood vessel passing through the underside area Sv of the probe 10 can be readily detected. Thus, the blood vessel position detection precision can be improved.

Then, the ultrasonic array switching circuit 21 in the biological testing device 1 switches one of the four ultrasonic arrays in the probe 10 to operable status so as to be able to transmit and receive ultrasonic waves. As a result, there is no noise from ultrasonic waves transmitted from other ultrasonic arrays, and no reception signals are detected based on ultrasonic waves received from other ultrasonic arrays. Thus, by obtaining TOF data from the timing for outputting ultrasonic waves from the ultrasonic arrays 12 to the timing for outputting reception signals, the central processing circuit 29 can calculate the exact reflection position of ultrasonic waves based on TOF data, position data on the various ultrasonic arrays, and transmission angle data for the ultrasonic waves. Because a blood vessel can be considered to be positioned along a straight line within a very small area, the exact position of a blood vessel can be measured if an exact reflection position can be determined at two points as described above.

Second Embodiment

The following is an explanation with reference to the drawings of the biological testing device in the second embodiment of the present invention.

The biological testing device in the second embodiment has an ultrasonic array 12 configuration that is a variation on the biological testing device in the first embodiment. The rest of the configuration is identical to the one in the biological testing device of the first embodiment.

Figure 11:
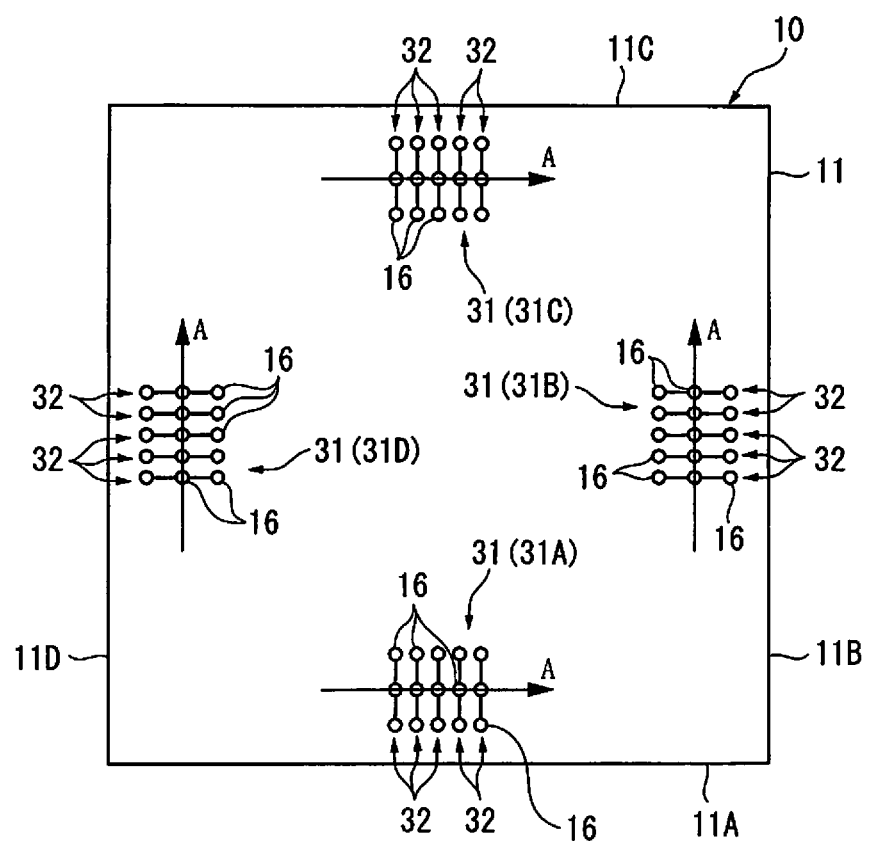
FIG. 11 is a top view of the substrate surface of the probe in the biological testing device in the second embodiment of the present invention.

FIG. 11 is a top view of the substrate 11 of the probe 10 in the biological testing device in the second embodiment of the present invention. In FIG. 11, the biological testing sensor 13 has been omitted. In the explanation of the second and subsequent embodiments, an explanation of the components with the same numbers has been omitted or simplified in configurations similar to the first embodiment.

As in the first embodiment, ultrasonic arrays 31 (31A, 31B, 31C, 31D) are arranged in the central position of each side 11A-11D of the substrate 11 in the probe 10 of the biological testing device of the second embodiment.

Here, in the ultrasonic arrays 31 of the second embodiment, a plurality of ultrasonic elements 32 is arranged in a linear scanning direction A, and the direction of the corresponding sides 11A-11D is the same direction as the linear scanning direction A. Also, the ultrasonic elements 32 have a plurality of ultrasonic transducers 16 (three in this embodiment) which are arranged in the perpendicular scanning direction which is perpendicular to the linear scanning direction A. The configuration of the ultrasonic transducers 16 is similar to the ultrasonic elements 32 in the first embodiment, so further explanation has been omitted.

In a single ultrasonic element 32, the upper electrode wires 153A of the ultrasonic transducers 16 can be connected to each other as a shared electrode, and the lower electrode wires 151A connected to the lower electrodes 151 of the ultrasonic transducers 16 can be connected independently. In other words, the ultrasonic transducers 16 are designed so as to be able to operate independently.

In a single ultrasonic array 31, all of the upper electrode wires 153A can also be connected to form a shared electrode wire.

In such an ultrasonic array 31, the ultrasonic waves can be focused on a predetermined point by controlling the ultrasonic wave output timing of the various ultrasonic transducers 16 in the ultrasonic elements 32. This enlarges the Fresnel zone in which the ultrasonic waves can be outputted as plane waves, and extends the distance in which the ultrasonic waves can be propagated as plane waves.

Figure 12:
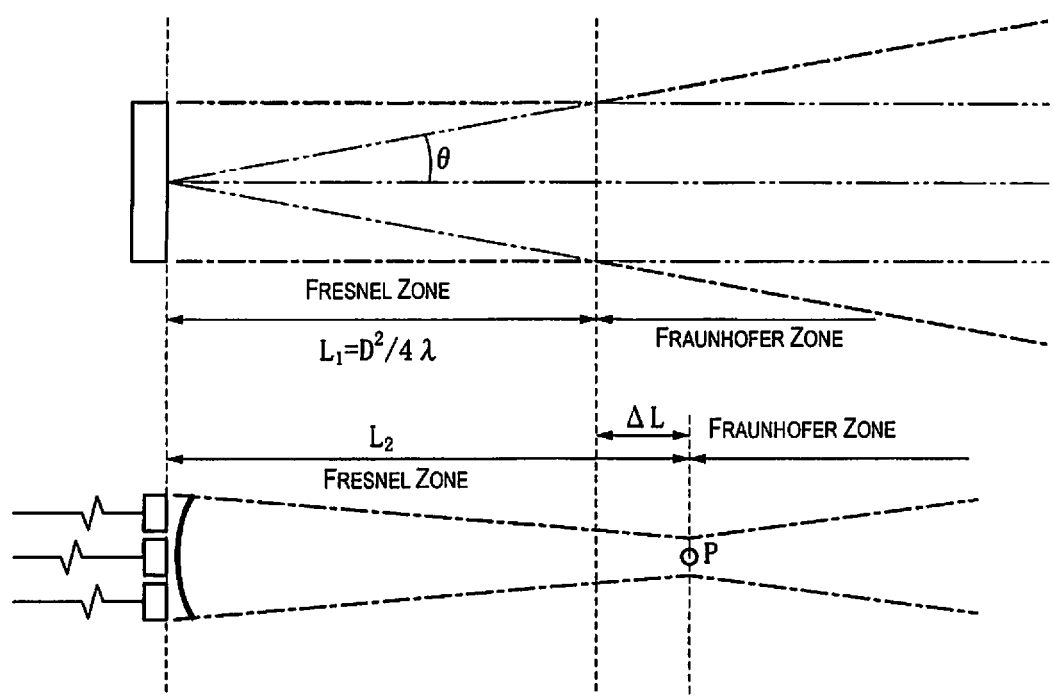
FIG. 12 is a diagram showing the difference between the Fresnel zone in the ultrasonic array and the Fraunhofer zone outputted from a single ultrasonic transducer in the second embodiment.

FIG. 12 is a diagram showing the difference between the Fresnel zone for the ultrasonic waves outputted from a single ultrasonic transducer (upper figure) and the Fraunhofer zone for the ultrasonic array (lower figure) in the second embodiment.

As shown in the upper figure in FIG. 12, the ultrasonic waves transmitted from a single ultrasonic transducer 16 as shown in the first embodiment have a Fresnel zone extending to a distance of $L1=D^2/4\lambda$ and are propagated as plane waves. In contrast, as shown in the lower figure in FIG. 12, the timing for transmitting the ultrasonic waves from the ultrasonic element 32 in the center is delayed compared to the timing for transmitting the ultrasonic waves from the ultrasonic elements 32 on both ends. As a result, the synthesized waves from the ultrasonic waves outputted from each ultrasonic transducer 16 are focused on focal point P according to the delay period. In other words, by controlling the ultrasonic wave transmission timing for the various ultrasonic transducers 16, the position of focal point P can be controlled, and the distance of the Fresnel zone (i.e., the distance the ultrasonic waves can be propagated as plane waves) L2 can be adjusted to the desired distance.

Control of the delay period can be performed by the central processing circuit 29, the delay period calculating unit 27, and the signal delay circuit 25. The following is a description of the calculation method for this delay period, made with reference to FIG. 13.

Figure 13:
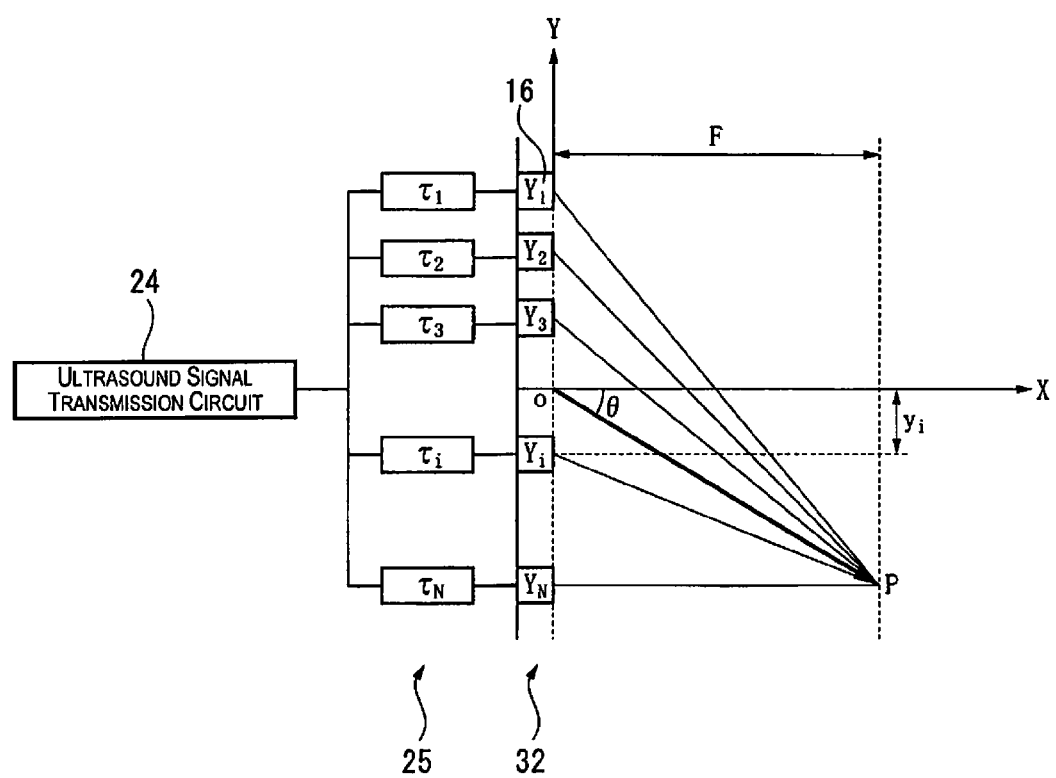
FIG. 13 is a diagram showing the ultrasonic waves transmitted by a plurality of ultrasonic transducers focused into single predetermined point.

FIG. 13 is a diagram showing the ultrasonic waves transmitted by a plurality of ultrasonic transducers 16 focused into single predetermined point. As shown in FIG. 13, 1-N ultrasonic transducers 16 are arranged. When the ultrasonic waves are focused on focal point P by adjusting the ultrasonic wave transmission timing for the ultrasonic transducers 16, the time τ(i, F) required for ultrasonic waves to reach the focal point P from the ultrasonic transducer 16 at given point Yi can be expressed by Equation (5) below.

Equation (5)

$$\tau(i, F) = \sqrt{\frac{(yi - F\tan\theta)^2 + F^2}{c}} \qquad (5)$$

As shown in FIG. 13, Equation (5) is an arithmetic expression for a situation in which the center point of an ultrasonic element 32 is the origin point (0, 0), the ultrasonic transducer 16 is arranged along the y axis, and the ultrasonic waves are transmitted in the x direction. In Equation (5), F is the x coordinate position of the focal point, and θ is the angle formed by the x axis and a straight line passing through the center point (origin point) of the ultrasonic element 32 and focal point P.

In the biological testing device of the second embodiment, the central processing circuit 29, the delay time calculating unit 27, and the signal delay circuit 25 control the output timing for the drive signals applied to the ultrasonic transducers 16 and delay the transmission timing of the ultrasonic waves based on Equation (5).

In other words, in the biological testing device of the second embodiment, the central processing circuit 29 sets the focal point P for the ultrasonic waves based on the depth at which the blood vessel is positioned, and outputs the point to the delay period calculating unit 27. The delay period calculating unit 27 calculates the delay period based on Equation (5) for focusing the ultrasonic waves outputted from the ultrasonic transducers 16 and inputs the delay period to the signal delay circuit 25.

Here, the depth at which the blood vessel is positioned is inputted by the user using the operating unit 5. For example, when the object to be detected is a blood vessel in a finger which is a short distance from the skin, and input signals for this testing target have been inputted by the user using the operating unit 5, the central processing circuit 29 outputs a small F value (distance to the focal point P) to the delay period calculating unit 27. When the object to be detected is a blood vessel in an arm which is a long distance from the skin, and input signals indicating that the arm is to be the testing target have been inputted by the user using the operating unit 5, the central processing circuit 29 outputs a larger F value to the delay period calculating unit 27. When the site to be detected is a leg or other part where the distance from the skin to the blood vessel is even longer, and input signals indicating that the leg is to be the testing target have been inputted by the user using the operating unit 5, the central processing circuit 29 outputs an even larger F value to the delay period calculating unit 27. Here, the F values are preset so that values stored in the storage unit 28 can be used. When the testing target is a finger, the ultrasonic wave transmission timing from the ultrasonic transducers 16 constituting an ultrasonic element 32 is not delayed. As in the first embodiment, the blood vessel position can be detected within the Fresnel zone.

Operations and Effects of Second Embodiment

In the biological testing device of the second embodiment, the ultrasonic arrays 31 have ultrasonic elements 32 in a one-dimensional array arranged in the linear scanning direction A, and the ultrasonic elements 32 have ultrasonic transducers 16 arranged in the perpendicular scanning direction perpendicular to their linear scanning directions A. The delay period calculating unit 27 and the signal delay circuit 25 output drive signals to the ultrasonic transducers 16 arranged in the perpendicular scanning direction of the ultrasonic elements 32 based on the optimum F value inputted from the central processing circuit 29 so as to delay the ultrasonic wave transmission timing from the ultrasonic transducers 16 on both ends to the ultrasonic transducer 16 in the center.

As a result, the distance of the Fresnel zone for the ultrasonic waves transmitted from the ultrasonic transducers 16 (i.e., the distance in which the ultrasonic waves are propagated as plane waves) L2 can be extended compared to using a single ultrasonic transducer 16, and the scan area Sarea for the blood vessel position can be enlarged. Thus, the biological testing device can measure the position of blood vessels in a wider area.

Third Embodiment

The following is an explanation with reference to the drawings of the biological testing device in the third embodiment of the present invention.

The biological testing device in the second embodiment has an ultrasonic array 12 configuration that is a variation on the biological testing device in the first embodiment. The rest of the configuration is identical to the one in the biological testing device of the first embodiment.

Figure 14:
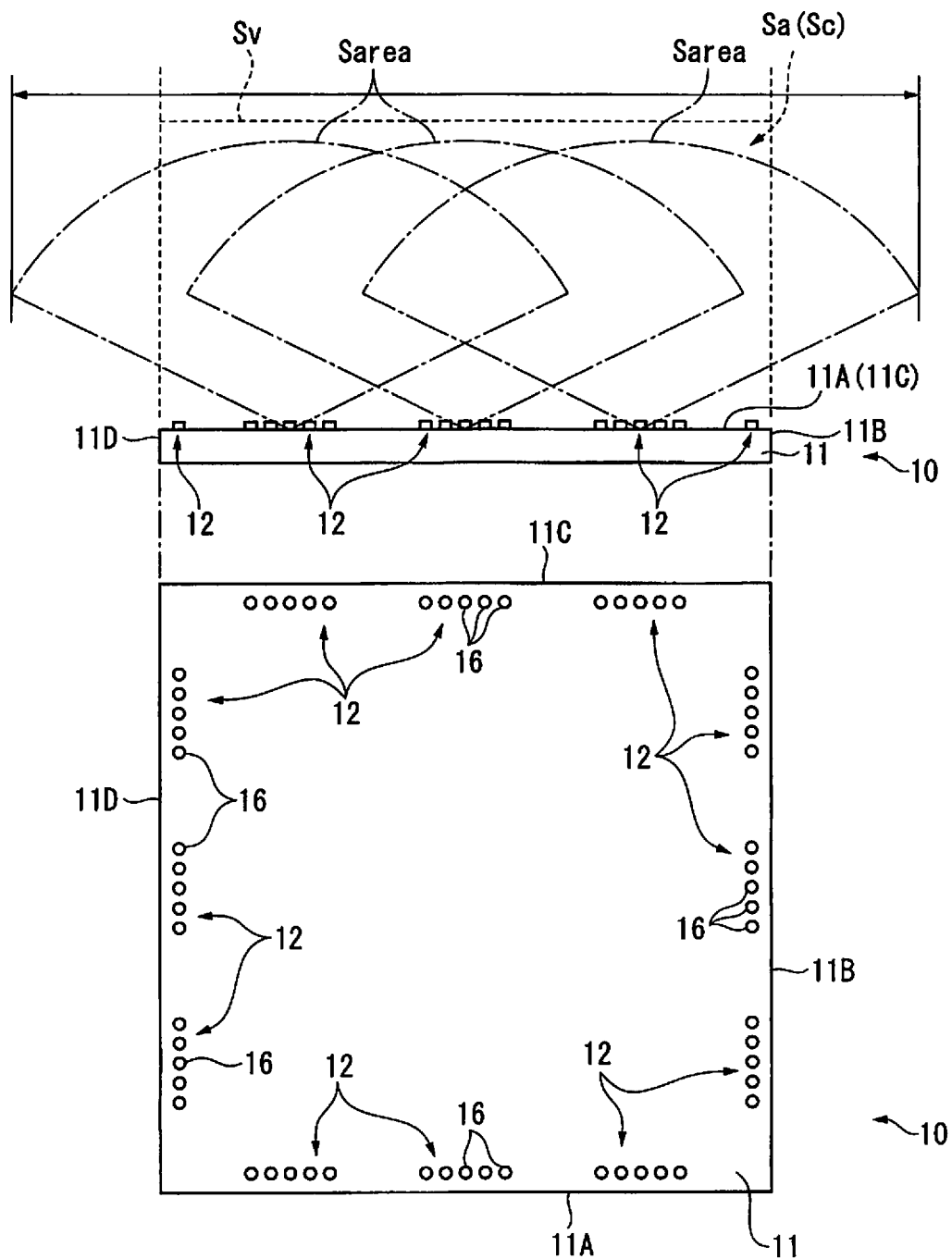
FIG. 14 is a cross-sectional view and a top view showing a simplified configuration of the probe in the third embodiment of the present invention.

FIG. 14 is a cross-sectional view and a top view showing a simplified configuration of the probe 10 in the third embodiment of the present invention.

In the biological testing device of the third embodiment, three ultrasonic arrays 12 are arranged on each side 11A-11D of the substrate 11 of the probe 10. These ultrasonic arrays 12 are arranged at positions apart from one another, and wiring patterns for a biological testing sensor not shown in the drawing and wiring patterns for the ultrasonic arrays 12 are formed in the spaces between ultrasonic arrays 12.

Here, as mentioned above, the ultrasonic arrays 12 have a substantially fan-shaped area Sarea within the scan planes S. Thus, a scan area Sarea covering the sides 11A-11D of the substrate 11 can be formed by arranging a plurality of ultrasonic arrays 12 on one side. The side planes Sa, Sb, Sc, Sd of the underside area Sv of the probe 10 for a more reliable scan area Sarea, and a blood vessel passing through the underside area Sv of the probe can be detected more reliably and more accurately.

In such a probe 10, a scan area Sarea extending beyond the underside area of the probe 10 can be formed using an ultrasonic array 12 arranged on both ends of each side 11A-11D. Thus, even when a blood vessel has shifted slightly from the underside area Sv of the probe, its position can still be detected by the ultrasonic arrays 12.

As described above, the biological testing device in the third embodiment can form a scan area Sarea that is wider and can more accurately detect blood vessels in a wider area than a probe 10 in which only one ultrasonic array 12 is formed on each side 11A-11D.

In the third embodiment, three ultrasonic arrays 12 were arranged on each side of the substrate 11. However, two ultrasonic arrays 12 or four ultrasonic arrays 12 can also be arranged on each side. Even when four or more ultrasonic arrays 12 are arranged on each side, they are arranged in positions apart from one another. As a result, wiring patterns for a biological testing sensor not shown in the drawings can be formed in the spaces between the ultrasonic arrays 12. This allows complicated wiring patterns to be avoided.

Fourth Embodiment

Figure 15:
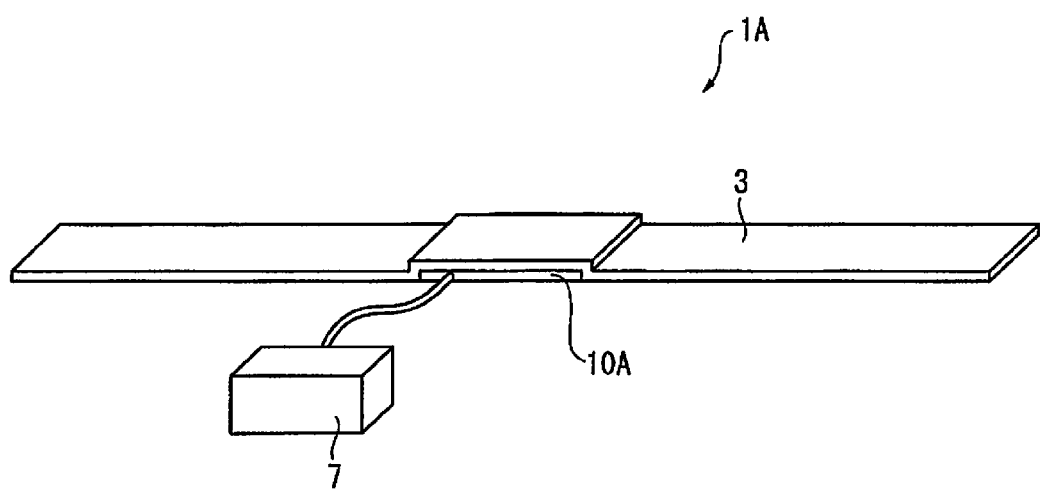
FIG. 15 is a perspective view showing an outline of the biological testing system in the fourth embodiment of the present invention.

The following is an explanation with reference to the drawings of the biological testing system 1A in the fourth embodiment of the present invention. FIG. 15 is a perspective view showing an outline of the biological testing system 1A in the fourth embodiment of the present invention.

Figure 16:
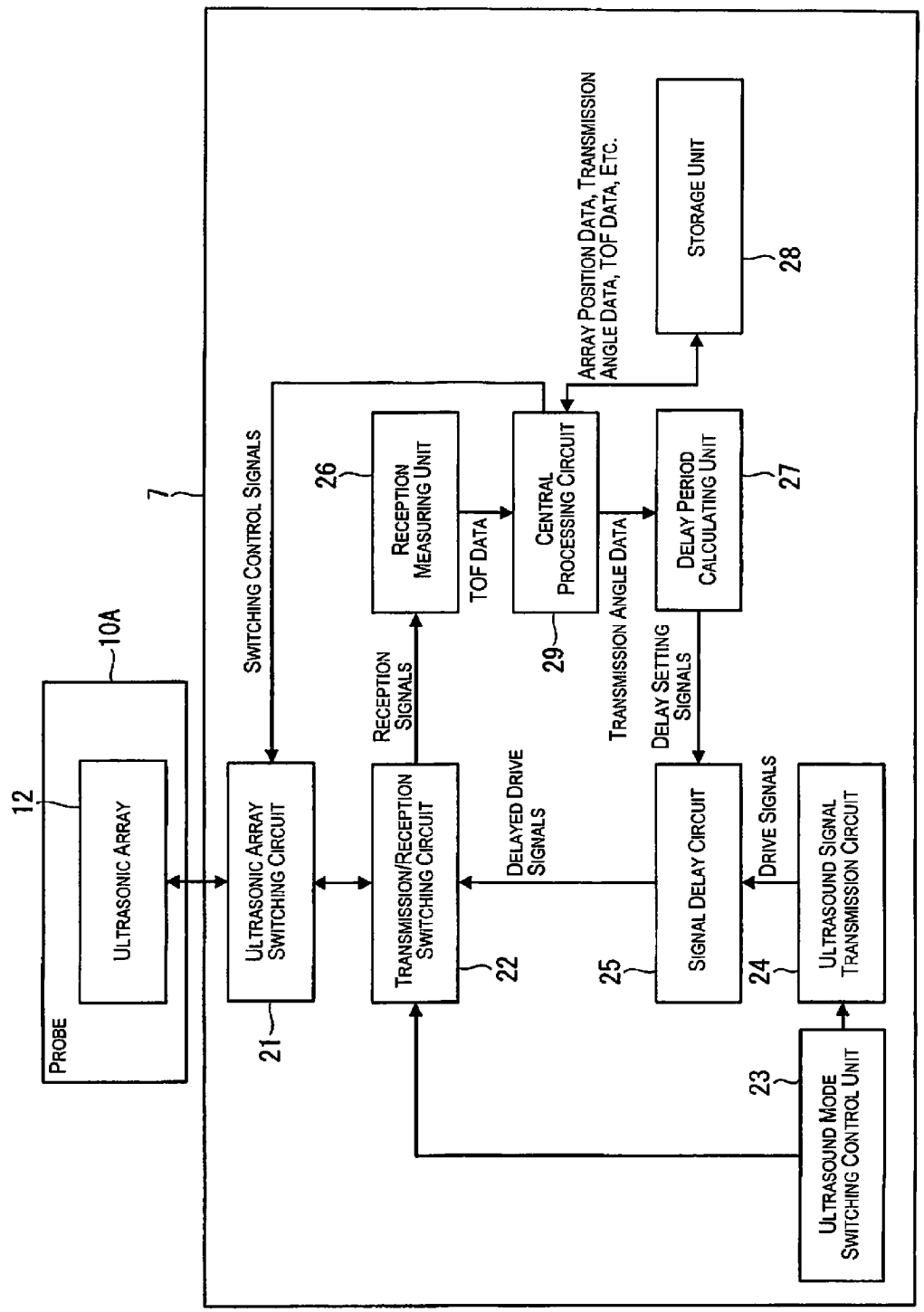
FIG. 16 is a block diagram showing a simplified configuration of the biological testing system in the fourth embodiment.

The biological testing system 1A of the fourth embodiment in FIG. 15 has a probe 10A, a band 3, and a control device 7. FIG. 16 is a block diagram showing a simplified configuration of the biological testing system 1A in the fourth embodiment.

In the biological testing system 1A, a probe 10A formed in a film shape is secured to a predetermined testing position on the body using a band, and signals outputted from the probe 10A are processed by the control device 7. As shown in FIG. 16, the control device 7 incorporates an ultrasonic array switching circuit 21, a transmission/reception switching circuit 22, an ultrasound mode switching control unit 23, an ultrasound signal transmission circuit 24, a signal delay circuit 25, a reception measuring unit 26, a delay period calculating unit 27, a storage unit 28, and a central processing circuit 29.

Because configuration in which the control device 7 is disposed is similar to the first embodiment, further explanation has been omitted.

In this configuration, an operating unit 5 and a display unit 4 are disposed in the control device 7 to allow the user to operate the biological testing system 1A. However, an operating unit 5 and a display unit 4 can also be connected to the control device 7.

In FIG. 15, the control device 7 is connected by a wire to the probe 10A. However, it can also be configured for wireless communication such as infrared, BLUETOOTH® or radio communication. In this case, a wireless communication unit for wireless communication is disposed in both the probe 10A and the control device 7. This configuration allows for a biological testing system 1A with superior portability and convenience because there is no wire to obstruct the attachment of the probe 10A.

Because only a thin probe 10A is attached to the body in the biological testing system 1A of the fourth embodiment, the biological testing system 1A does not obstruct the long-term measurement of blood vessel conditions and the weight of the unit does not become a physical burden. Therefore, changes in blood vessel conditions can be monitored while users go about their normal lives.

Other Embodiments

The present invention is not intended to be limited to the embodiments described above. It includes all variations and improvements within the scope of achieving the objectives of the present invention.

For example, in the first through fourth embodiments, the measurement device was a biological testing device 1 for measuring blood vessels in the body. However, the present invention is not limited to these embodiments. For example, an object to be tested having an acoustic impedance difference from the housing can be disposed inside a housing able to transmit ultrasonic waves, and the present invention can be applied to any measuring device for measuring the position of the object to be tested. For example, the present invention can be applied to a tube detection device for detecting the position of a tube inside a liquid.

Also, in the first through fourth embodiments, the ultrasonic transducers 16 were composed of a film-shaped lower electrode 151, a piezoelectric film 152, and an upper electrode 153 laminated on top of a support film 14. However, the present invention is not limited to these embodiments. For example, a bulk-shaped piezoelectric body can be arranged on top of a support film 14. Here, the bulk-shaped piezoelectric body is easily cut-molded into a rectangular shape, and a plurality of these piezoelectric bodies are arranged in the linear scanning direction A, and longitudinally in the perpendicular scanning direction.

Also, in the first through fourth embodiments, the diaphragms 141 serving as the ultrasonic transducers 16 are round shaped, and round piezoelectric bodies 15 are formed. However, the present invention is not limited to these embodiments. For example, rectangular or polygonal piezoelectric bodies 15 can be disposed in rectangular or polygonal diaphragms 141. In other words, the ultrasonic transducers 16 can have any shape as long as there is stress balance when the diaphragms 141 are vibrating.

Also, in the first through fourth embodiments, the substrate 11 of the probe 10 is rectangular (or square). However, the present invention is not limited to these embodiments. For example, the substrate can be polygonal, round or oval-shaped. When the substrate 11 is polygonal, ultrasonic arrays 12 can be arranged on each side. When the substrate is round or oval-shaped, the ultrasonic arrays are arranged so that the linear scanning direction A is in a tangential direction with respect to the substrate 11, and so that the position of blood vessels passing through the underside area of the probe 10 can be measured.

Also, in the first through fourth embodiments, ultrasonic arrays 12 are disposed along each side 11A-11D. However, two acoustic arrays 12 with different linear scanning direction A can be arranged apart from each other in predetermined positions on the plane of the substrate 11. Here, when a blood vessel passes through the scan area Sarea formed by the ultrasonic arrays 12, the position of the blood vessel can be measured. However, when a blood vessel does not pass through the scan area Sarea, the orientation and/or the attachment position of the biological testing device 1 has to be changed.

As a result, at least three ultrasonic arrays 12 are preferably disposed in the biological testing device 1. In this way, when two ultrasonic arrays can only detect the reflection position at one point, the other ultrasonic array can detect the reflection position at the remaining point, and the position of the blood vessel can be identified. More preferably, the ultrasonic arrays 12 are arranged on the plane of the substrate 11 so that a closed area surrounded by the linear scanning directions A of three or more ultrasonic arrays 12 is formed. In other words, a blood vessel passing through the underside area of the closed area can be reliably detected if a closed area is formed, and the blood vessel detection precision can be further improved.

In the first through fourth embodiments, the biological testing sensor 13 for conducting biological testing is disposed on the substrate 11. However, the present invention is not limited to these embodiments. For example, the biological testing sensor can be formed on top of another substrate.

Also, for example, a round window can be formed on top of the substrate 11, and a biological testing sensor can be disposed rotatably inside the round window. In this configuration, the biological testing sensor can be rotated based on the measurement results for the blood vessel position after the position of the blood vessel has been measured. Here, the position of the blood vessel and the axial direction of the blood vessel can be displayed on the display unit 4, and the biological testing sensor rotated based on the display. In this way, the biological testing sensor can be aligned in the axial direction of the blood vessel and measurements easily taken even by a person without technical expertise.

In the second embodiment, the position at which the biological testing device 1 is attached is set and inputted. The optimum F value is selected by the central processing circuit 29 and outputted to the delay period calculating unit 27. The delay period for the drive signals outputted to the ultrasonic transducers 16 constituting the ultrasonic elements 32 is then calculated by the delay period calculating unit 27. However, the present invention is not limited to this embodiment. For example, the delay period can be calculated by the delay period calculating unit 27 based on preset optimum F values for a preset position for testing blood vessel conditions in, for example, a biological testing device 1 specially adapted for testing the blood vessel conditions in an arm.

Figure 17:
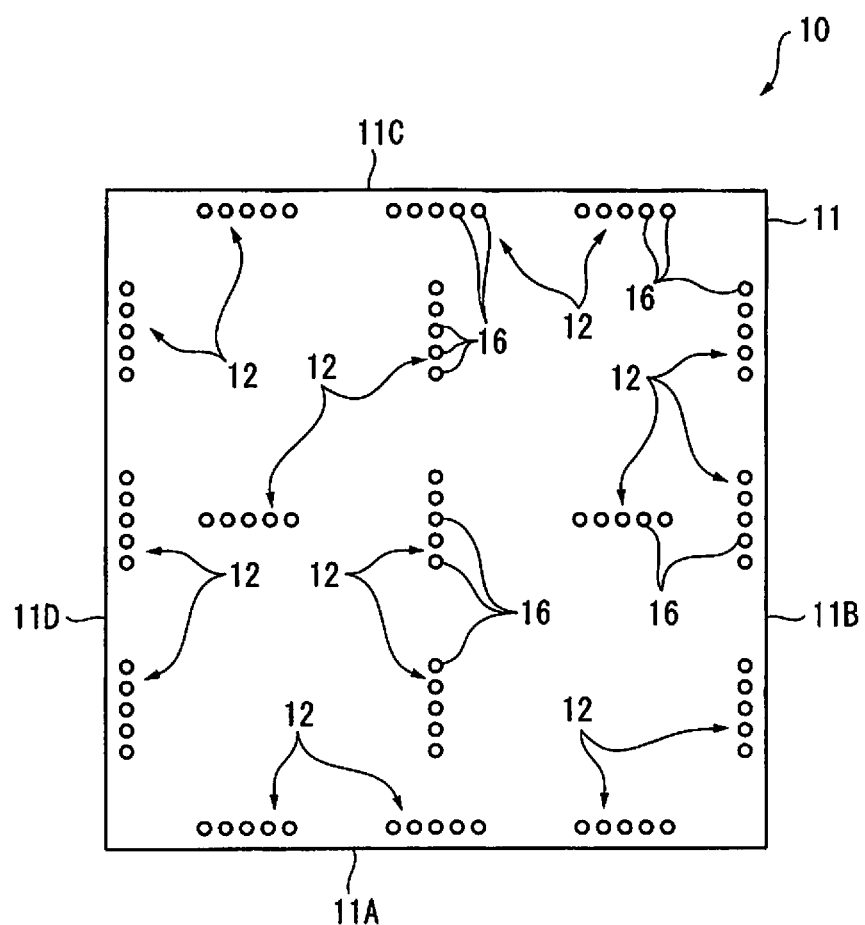
FIG. 17 is a top view showing a simplified configuration of the probe in another embodiment.

Also, in the third embodiment, a plurality of ultrasonic arrays 12 is arranged on each side 11A-11D. However, the present invention is not limited to this embodiment. For example, as shown in FIG. 17, a plurality of ultrasonic arrays 12 can be arranged not only along each side 11A-11D of the substrate 11, but a region within the plane of the substrate 11. Here, because a larger amount of TOF data can be obtained from the ultrasonic arrays 12, the position of a blood vessel can be measured more accurately based on the TOF data. In this case, for example, the axial position of a blood vessel can be determined more accurately even when the blood vessel bends in the underside area Sv of the probe 10.

Figure 18:
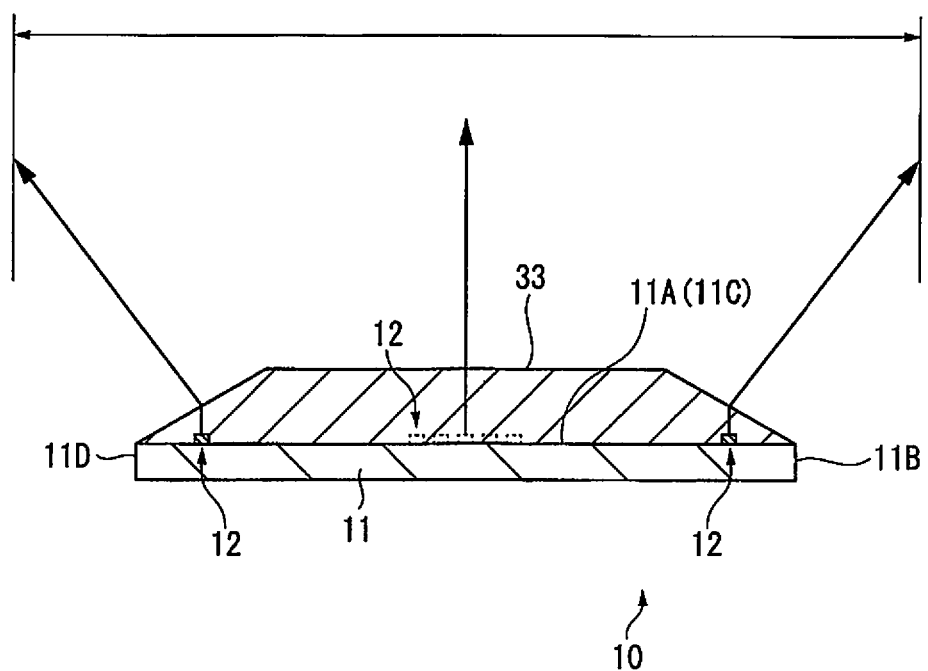
FIG. 18 is a sectional view showing a simplified configuration of the probe in yet another embodiment.

Also, in the third embodiment, the arrangement of a plurality of ultrasonic arrays 12 on each side 11A-11D forms a scan area Sarea covered by each side 11A-11D. However, as shown in FIG. 18, the scan area Sarea can be enlarged by forming an acoustic refraction layer 33 on the substrate 11 of the probe 10. This acoustic refraction layer 33 faces the acoustic array 12 in the center and has a surface parallel to the substrate 11. It also has an inclined surface facing the ultrasonic arrays 12 on both ends, which is inclined towards both ends of the substrate 11. The material used in the acoustic refraction layer 33 has a sound propagation speed greater than that of the body. Because the speed of sound in the body is 1530 m/s, silicon (speed of sound: 8400 m/s), quartz (speed of sound: 5900 m/s), glass (speed of sound: 4000-5300 m/s), nylon (speed of sound: 2600 m/s), polystyrene (speed of sound: 2350 m/s), or polyethylene (speed of sound: 1900 m/s) can be used.

By using an acoustic refraction layer 33, a scan area Sarea can be formed in which the ultrasonic waves outputted from the ultrasonic arrays 12 positioned on both ends of each side 11A-11D spread outward from the probe underside area. As a result, blood vessels located in a wider area can be detected by the probe 10 in the biological testing device of the third embodiment.

In the fourth embodiment, the control device 7 incorporates an ultrasonic array switching circuit 21, a transmission/reception switching circuit 22, an ultrasound mode switching control unit 23, an ultrasound signal transmission circuit 24, a signal delay circuit 25, a reception measuring unit 26, a delay period calculating unit 27, a storage unit 28, and a central processing circuit 29. However, the present invention is not limited to this. For example, an ultrasonic array switching circuit 21, a transmission/reception switching circuit 22, and a signal delay circuit 25 can be disposed in the probe 10A. When these circuits are included in the probe 10A, the increase in the thickness of the probe 10A can be reduced by, for example, forming them on the substrate 11. Here, the probe 10A constitutes the ultrasonic sensor of the present invention, and the control device 7 communicating with the probe 10A constitutes the measurement system of the present invention.

In the measurement system in this variation and in the biological testing system 1A in the fourth embodiment, the control device 7 can send data to a server device connected, for example, via the Internet. This allows personnel at a medical establishment such as a hospital to continuously monitor the blood vessel conditions in the patient wearing the probe 10A.

In the first through fourth embodiments, the ultrasonic arrays 12 send and receive ultrasonic waves via the ultrasonic transducers 16, and the ultrasound mode switching control unit 23 switches between the ultrasound transmission mode and the ultrasound reception mode. However, the present invention is not limited to these embodiments.

For example, the ultrasonic transducers 16 constituting the ultrasonic arrays 12 can include odd-numbered ultrasonic transducers 16 used as ultrasound transmitting elements, and even-numbered ultrasonic transducers 16 used as ultrasound receiving elements. Also, ultrasonic waves can be transmitted from the ultrasonic transducers 16 at one end of the line in an ultrasonic array 12, and the ultrasonic waves can be received by the ultrasonic transducers 16 at the other end of the line.

Also, special units can be created which include a dedicated ultrasonic transducer for transmitting ultrasonic waves, and a dedicated ultrasonic transducer for receiving ultrasonic waves.

Here, an ultrasonic wave transmission array in which a plurality of dedicated ultrasonic transducers for transmitting ultrasonic waves are arranged linearly can be arranged parallel to an ultrasonic wave reception array in which a plurality of dedicated ultrasonic transducers for receiving ultrasonic waves are arranged linearly.

In the embodiments described above, the delay period calculating unit 27 calculates the delay period for the drive signals inputted to the various ultrasonic transducers 16 by receiving transmission angle data from the central processing circuit 29. In other words, the delay period calculating unit 27 is configured as hardware. However, the present invention is not limited to these embodiments. For example, a delay period calculating program is stored in the storage unit 28, and the central processing circuit 29 retrieves and executes the delay period calculating program to calculate the delay period for the various drive signals. Also, in these embodiments, the reflection position calculating unit and the position calculating unit of the present invention were functions in which the central processing circuit 29 retrieves and executes a reflection position calculating program and a blood vessel position measuring program. However, the reflection position calculating unit and the position calculating unit can be configured as hardware using integrated circuits (ICs).

The best configurations for carrying out the present invention were described above in detail, but the present invention is not limited to these configurations. In other words, the present invention was illustrated and explained with reference to specific embodiments. However, a person of ordinary skill in the art could make various modifications and improvements to the embodiments described above without departing from the scope of the technical ideas and objectives of the present invention.

General Interpretation of Terms

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. An ultrasonic sensor comprising:
a substrate having a surface and a plurality of sides such that the surface is disposed between the sides;
three or more ultrasonic arrays disposed on the surface of the substrate; and
a control unit configured to control ultrasonic waves transmitted from the ultrasonic arrays,
each of the three or more ultrasonic arrays including a linear array structure in which a plurality of ultrasonic elements are aligned in an alignment direction in a corresponding one of three or more straight lines, with the three or more straight lines collectively enclosing a single closed area on a plane that contains the surface of the substrate, the linear array structure having a length in the alignment direction, the length being less than a distance in the alignment direction between one edge of the linear array structure in the alignment direction and one of the sides of the substrate, which is closest to the one edge in the alignment direction, the single closed area having a polygonal shape, the three or more straight lines partially defining different sides of the polygonal shape of the single closed area, respectively,
the control unit being configured to control the ultrasonic waves transmitted from each of the three or more ultrasonic arrays so that the ultrasonic waves are transmitted within a scanning plane that contains the corresponding one of the three or more straight line and that is perpendicular to the surface of the substrate.

2. The ultrasonic sensor according to claim 1, wherein
the control unit is configured to control a transmission angle of the ultrasonic waves transmitted from each of the three or more ultrasonic arrays by controlling a timing for transmitting the ultrasonic waves from each of the ultrasonic elements.

3. The ultrasonic sensor according to claim 1, wherein
the substrate is formed in the polygonal shape,
each of the three or more straight lines is arranged along a corresponding one of sides of the polygonal shape of the substrate near a periphery portion spaced apart from a center position of the polygonal shape of the substrate.

4. The ultrasonic sensor according to claim 3, wherein
at least two of the three or more ultrasonic arrays are arranged apart from each other with respect to each of the sides of the substrate.

5. The ultrasonic sensor according to claim 3, wherein
each of the three or more straight lines is arranged parallel to the corresponding one of the sides of the polygonal shape of the substrate.

6. The ultrasonic sensor according to claim 1, wherein
at least two of the three or more straight lines are perpendicular to each other.

7. The ultrasonic sensor according to claim 6, wherein
the control unit is configured to delay the timings at which the ultrasonic waves are transmitted from end ultrasonic elements arranged at both ends towards a center ultrasonic element arranged in a center portion, among the ultrasonic elements aligned in one of the three or more straight lines.

8. A measuring device comprising the ultrasonic sensor according to claim 1.

9. The measuring device according to claim 8, further comprising
a central processing circuit configured to switch the ultrasonic arrays among the ultrasonic arrays into which and from which ultrasonic waves are transmitted and received, configured to calculate a reflection position at which the ultrasonic waves are reflected based on reflected ultrasonic waves detected by the ultrasonic arrays, and configured to calculate the position of an object to be detected from the reflection position.

10. A measurement system comprising the ultrasonic sensor according to claim 1.

11. The measurement system according to claim 10, further comprising
a control device connected to the ultrasonic sensor to communicate with the ultrasonic sensor, wherein
the ultrasonic sensor is configured and arranged to transmit to the control device reception signals based on reflected ultrasonic waves detected by the three or more ultrasonic arrays, and to drive the three or more ultrasonic arrays based on drive signals inputted from the control device, and
the control device includes a central processing circuit that is configured to calculate a reflection position at which the ultrasonic waves are reflected based on the reception signals transmitted from the ultrasonic sensor, and configured to calculate a position of an object to be detected from the reflection position.

12. A probe comprising:
a substrate having a surface and a plurality of sides such that the surface is disposed between the sides; and
three or more ultrasonic arrays disposed on the surface of the substrate,
each of the ultrasonic arrays including a linear array structure in which a plurality of ultrasonic elements are aligned in an alignment direction in a corresponding one of three or more straight lines, with the three or more straight lines collectively enclosing a single closed area on a plane that contains the surface of the substrate, the linear array structure having a length in the alignment direction, the length being less than a distance in the alignment direction between one edge of the linear array structure in the alignment direction and one of the sides of the substrate, which is closest to the one edge in the alignment direction, the single closed area having a polygonal shape, the three or more straight lines partially defining different sides of the polygonal shape of the single closed area, respectively.

13. The probe according to claim 12, wherein
the substrate is formed in the polygonal shape,
each of the three or more straight lines is arranged along a corresponding one of sides of the polygonal shape of the substrate near a periphery portion spaced apart from a center position of the polygonal shape of the substrate.

14. The probe according to claim 12, wherein
each of the three or more straight lines is arranged parallel to the corresponding one of the sides of the polygonal shape of the substrate.

15. The probe according to claim 12, wherein
at least two of the three or more ultrasonic arrays are arranged apart from each other with respect to each of the sides of the substrate.

16. The probe according to claim 12, wherein at least two of the three or more straight lines are perpendicular to each other.

* * * * *